(12) United States Patent
Hayashi et al.

(10) Patent No.: US 8,829,247 B2
(45) Date of Patent: Sep. 9, 2014

(54) CYCLIC COMPOUND, METHOD OF PRODUCING THE SAME, RADIATION SENSITIVE COMPOSITION, AND METHOD OF FORMING RESIST PATTERN

(75) Inventors: Hiromi Hayashi, Hiratsuka (JP); Masatoshi Echigo, Hiratsuka (JP); Dai Oguro, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 42 days.

(21) Appl. No.: 13/500,715

(22) PCT Filed: Sep. 27, 2010

(86) PCT No.: PCT/JP2010/005796
§ 371 (c)(1),
(2), (4) Date: Jun. 19, 2012

(87) PCT Pub. No.: WO2011/043029
PCT Pub. Date: Apr. 14, 2011

(65) Prior Publication Data
US 2012/0251947 A1    Oct. 4, 2012

(30) Foreign Application Priority Data

Oct. 6, 2009 (JP) ................................. 2009-232529

(51) Int. Cl.
*C07C 43/23* (2006.01)
*C07C 41/30* (2006.01)
*C07C 39/17* (2006.01)

(52) U.S. Cl.
USPC ........... 568/717; 568/719; 568/720; 568/445; 560/81; 560/83

(58) Field of Classification Search
USPC ........... 568/719, 445, 717, 720, 7; 560/81, 83
See application file for complete search history.

(56) References Cited

U.S. PATENT DOCUMENTS

| | | | |
|---|---|---|---|
| 5,292,452 A | 3/1994 | Buchecker et al. | |
| 5,382,379 A | 1/1995 | Onji et al. | |
| 6,093,517 A * | 7/2000 | Ito et al. | 430/270.1 |
| 8,530,136 B2 * | 9/2013 | Bozano et al. | 430/270.1 |
| 2010/0047709 A1 | 2/2010 | Echigo et al. | |

FOREIGN PATENT DOCUMENTS

| | | |
|---|---|---|
| EP | 0 475 273 A1 | 3/1992 |
| EP | 0 750 028 A2 | 12/1996 |
| EP | 0 820 983 A1 | 1/1998 |
| GB | 2 111 992 A | 7/1983 |
| JP | H08-120270 A | 5/1996 |
| JP | H09-077703 A | 3/1997 |
| JP | 2003-321423 A | 11/2003 |
| JP | 2004-018421 A | 1/2004 |
| JP | 2005-326838 A | 11/2005 |
| JP | 2006-016342 A | 1/2006 |
| JP | 2008-116677 A | 5/2008 |
| JP | 2008-145539 A | 6/2008 |
| JP | 2009-149630 A | 7/2009 |
| JP | 2009-173623 A | 8/2009 |
| JP | 2011028270 A * | 2/2011 |
| WO | 2009/075308 A1 | 6/2009 |

OTHER PUBLICATIONS

Oizumi et al, Development of New Negative-tone Molecular Resists Baed on Calixarene for EUV Lithography, Journal of Photopolymer Science and Technology, vol. 21, No. 3, Jan. 1, 2008, pp. 443-449.*
Shoji Yamamoto et al. "The Reaction of Trialkylboranes With the α-Lithio Derivatives of Bis (Phenylthio) Methane and of 1, 1-Bis (Phenylthio) Pentane. A Convenient Method for the Preparation of Aldehydes and Ketones," Chemistry Letters published by the Chemical Society of Japan, No. 9, Jun. 23, 1973, p. 961-962 (2 pages).
Extended European Search Report issued in counterpart European Application No. 10 82 1707.6 dated May 2, 2013 (10 pages).
International Search Report from the International Bureau of WIPO for International Application No. PCT/JP2010/005796 dated Dec. 21, 2010 (2 pages) and an English translation of the same (2 pages).

* cited by examiner

*Primary Examiner* — Amanda C. Walke
(74) *Attorney, Agent, or Firm* — Fitch, Even, Tabin & Flannery LLP

(57) ABSTRACT

This invention addresses problems to provide a cyclic compound having a high solubility in safety solvents and a high sensitivity and being good in the shape of the resulting resist pattern, a method of producing the same, a radiation sensitive composition comprising the same, and a method of forming a resist pattern using the radiation sensitive composition. As means for solving the problem, there are provided a cyclic compound having a specific structure, a radiation sensitive composition comprising the compound, and a method of forming a resist pattern using the composition.

7 Claims, No Drawings

CYCLIC COMPOUND, METHOD OF PRODUCING THE SAME, RADIATION SENSITIVE COMPOSITION, AND METHOD OF FORMING RESIST PATTERN

CROSS-REFERENCE TO RELATED APPLICATIONS

This application is a U.S. national phase application filed under 35 U.S.C. §371 of International Application PCT/JP2010/005796, filed on Sep. 27, 2010, designating the United States, which claims priority from Japanese Application 2009-232529, filed Oct. 6, 2009, which are hereby incorporated herein by reference in their entirety.

TECHNICAL FIELD

This invention relates to a cyclic compound represented by a specific chemical structure which is useful as an acid-amplified, non-polymeric resist material, a radiation sensitive composition containing the cyclic compound, and a method of forming a resist pattern using such a composition.

BACKGROUND ART

Conventionally known general resist materials are polymer materials capable of forming amorphous thin film. For example, a solution of a polymer resist material such as polymethyl methacrylate, polyhydroxystyrene having an acid-dissociable reactive group, polyalkyl methacrylate or the like is applied onto a substrate to form a thin resist film, which is then irradiated with ultraviolet rays, far ultraviolet rays, electron beams, extreme ultraviolet rays (EUV), X-rays or the like to form line patterns having a width of about 45 to 100 nm.

However, the polymer resist compounds have a molecular weight as large as about 10,000 to 100,000 and a broad molecular weight distribution. Therefore, in the lithography using the polymer resist compound, roughness is caused on the surface of the fine pattern and it is difficult to control dimension of the pattern and hence the yield ratio lowers. In the lithography using the conventional polymer resist material, therefore, there is a limit in fine processing. To this end, various low molecular weight resist materials have been proposed for preparing finer patterns.

For example, there have been proposed an alkali-developable, negative-type radiation sensitive compositions using a low molecular weight, polynuclear polyphenol compound as a main component (see JP-A-2005-326838 and JP-A-2008-145539). However, there are drawbacks that these compositions are insufficient in the heat resistance and the shape of the resulting resist pattern becomes poor.

As the low molecular weight resist material are proposed alkali-developable, negative-type radiation-sensitive compositions using a low molecular weight, cyclic polyphenol compound as a main component (JP A-2009-173623 and T. Nakayama, M. Nomura, K. Haga, M. Ueda: Bull. Chem. Soc. Jpn., 71, 2979 (1998)).

These low molecular weight cyclic polyphenol compounds are expected to provide resist patterns being small in the molecular size, high in the resolution and small in the roughness because of their low molecular weights. In addition, the low molecular weight, cyclic polyphenol compound imparts a high heat resistance though it has a low molecular weight because of a rigid cyclic structure in its skeleton.

However, the conventionally known low molecular weight cyclic polyphenol compounds have several drawbacks that the solubility in safety solvents used in semiconductor production process is low, and the sensitivity is low, and the shape of the resulting resist pattern is bad. Therefore, it is desired to improve the low molecular weight cyclic polyphenol compounds.

SUMMARY OF THE INVENTION

It is an object of the invention to provide a cyclic compound having high solubility in safety solvents and a high sensitivity and being good in the shape of the resulting resist pattern, a method of producing the same, a radiation sensitive composition containing the same, and a method of forming a resist pattern using the radiation sensitive composition.

The inventors have devoted themselves to study for solving the above problems and found out that a cyclic compound having a specific structure is high in the solubility in safety solvents and high in the sensitivity and provides a good shape of a resist pattern, and as a result, the invention has been accomplished.

Namely, the invention is as follows.

1. A cyclic compound represented by the following formula (1):

[Chem. 1]

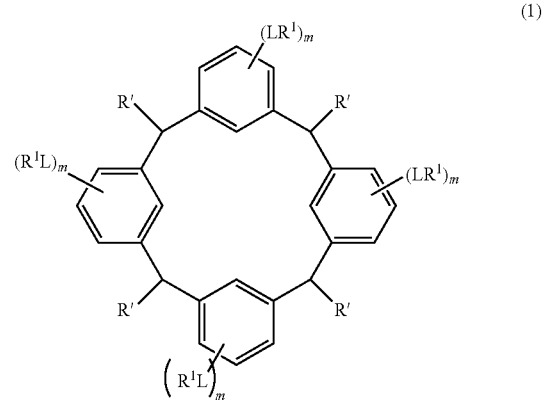

in the formula (1), L is independently a divalent group selected from the group consisting of a single bond, a linear or branched alkylene group having a carbon number of 1 to 20, a cycloalkylene group having a carbon number of 3 to 20, an arylene group having a carbon number of 6 to 24, —O—, —OC(=O)—, —OC(=O)O—, —N($R^5$)—C(=O)—, —N($R^5$)—C(=O)O—, —S—, —SO—, —SO$_2$—, and any combination thereof; $R^1$ is independently a functional group selected from the group consisting of an alkyl group having a carbon number of 1 to 20, a cycloalkyl group having a carbon number of 3 to 20, an aryl group having a carbon number of 6 to 20, an alkoxyl group having a carbon number of 1 to 20, cyano group, nitro group, hydroxyl group, heterocyclic group, halogen, carboxyl group, an acyl group having a carbon number of 2 to 20, an alkylsilyl group having a carbon number of 1 to 20 and a derivative thereof, or a hydrogen atom, with the proviso that at least one of $R^1$ is a hydrogen atom; R' is independently a group represented by the following formula (1-2):

[Chem. 2]

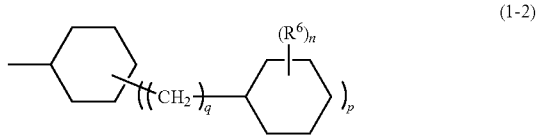

or a derivative thereof, $R^6$ is hydrogen or a functional group selected from the group consisting of an alkyl group having a carbon number of 1 to 12, a cycloalkyl group having a carbon number of 3 to 12, an aryl group having a carbon number of 6 to 12, an alkoxyl group having a carbon number of 1 to 12, cyano group, nitro group, heterocyclic group, halogen, carboxyl group, hydroxyl group and an alkylsilyl group having a carbon number of 1 to 12; $R^5$ is hydrogen or an alkyl group having a carbon number of 1 to 10; m is an integer of 1 to 4; n is an integer of 0 to 5; p is an integer of 0 to 5; and q is an integer of 0 to 5.

2. A cyclic compound according to the item 1, which is represented by the following formula (2):

[Chem. 3]

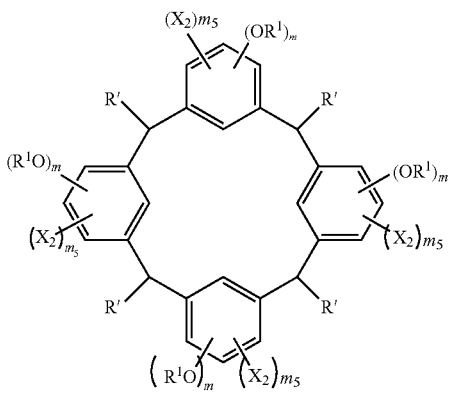

(2)

in the formula (2), $R^1$, R', p and m are the same as described above; $X_2$ is hydrogen or halogen atom; $m_5$ is a integer of 0 to 3; and $m+m_5=4$.

3. A cyclic compound according to the item 1, which is represented by the following formula (3):

[Chem. 4]

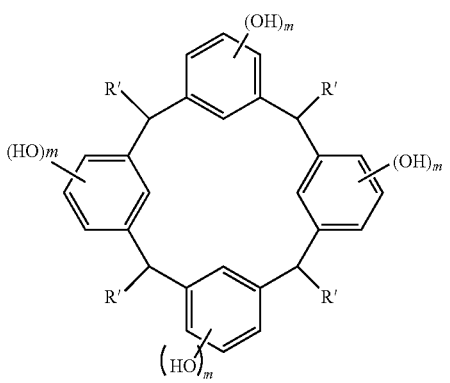

(3)

in the formula (3), R' and m are the same as described above.

4. A cyclic compound according to the item 1, wherein R' is independently represented by the following formula (1-4):

[Chem. 5]

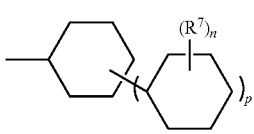

(1-4)

in the formula (1-4), $R^7$ is a functional group selected from the group consisting of an alkyl group having a carbon number of 1 to 12, a cycloalkyl group having a carbon number of 3 to 12, an aryl group having a carbon number of 6 to 12, an alkoxy group having a carbon number of 1 to 12, cyano group, nitro group, heterocyclic group, halogen, carboxy group, hydroxyl group, an alkylsilyl group having a carbon number of 1 to 12 and a derivative thereof; n is an integer of 0 to 5; and p is an integer of 0 to 5.

5. A cyclic compound according to the item 1, wherein R' is independently represented by the following formula (1-5):

[Chem. 6]

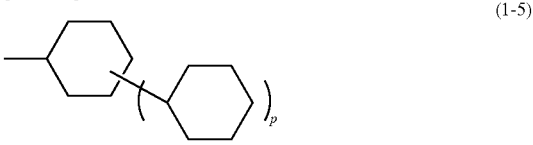

(1-5)

in the formula (1-5), p is an integer of 0 to 5.

6. A method of producing a cyclic compound represented by the formula (1), which comprises condensation reacting one or more selected from carbonyl compounds (A1) with one or more selected from phenolic compounds (A2).

7. A method of producing a cyclic compound represented by the formula (1), which comprises condensation reacting one or more selected from acetal compounds (A4) of carbonyl compounds (A1) with one or more selected from phenolic compounds (A2).

8. A radiation sensitive composition comprising a cyclic compound according to the item 1 and a solvent.

9. A radiation sensitive composition according to the item 8, wherein the cyclic compound is a cyclic compound synthesized by a condensation reaction of a compound having a carbon number of 2 to 59 and 1 to 4 formyl groups (aldehydic compound (A1A)) with a compound having a carbon number of 6 to 15 and 1 to 3 phenolic hydroxyl groups (phenolic compound (A2)), and having a molecular weight of 700 to 5000.

10. A radiation sensitive composition according to the item 8 comprising 1 to 80% by weight of a solid component and 20 to 99% by weight of a solvent.

11. A radiation sensitive composition according to the item 8, which further contains an acid generator (C) directly or indirectly generating an acid by irradiation of any radiation selected from the group consisting of visible light, ultraviolet ray, excimer laser, electron beams, extreme ultraviolet ray (EUV), X-ray and ion beams.

12. A radiation sensitive composition according to the item 8, which further contains an acid crosslinking agent (G).

13. A radiation sensitive composition according to the item 8, which further contains an acid-diffusion controller (E).

14. A radiation sensitive composition according to any one of the items 8 to 13, wherein the cyclic compound is a cyclic compound selected from the group consisting of compounds represented by the following formula (2-2):

[Chem. 7]

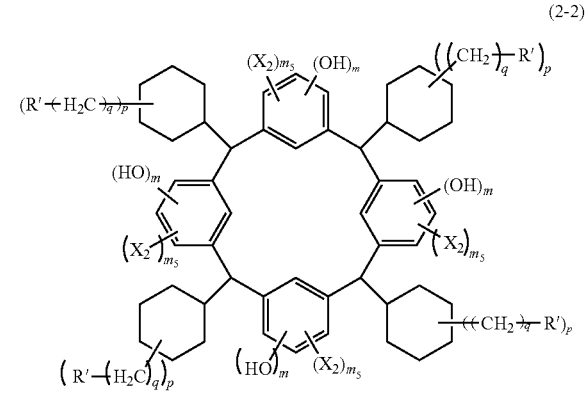

(2-2)

in the formula (2-2), R', $X_2$, p, q, m and $m_5$ are the same as described above.

15. A radiation sensitive composition according to the item 14, wherein the cyclic compound is a cyclic compound selected from the group consisting of compounds represented by the following formulae (4) or (5):

[Chem. 8]

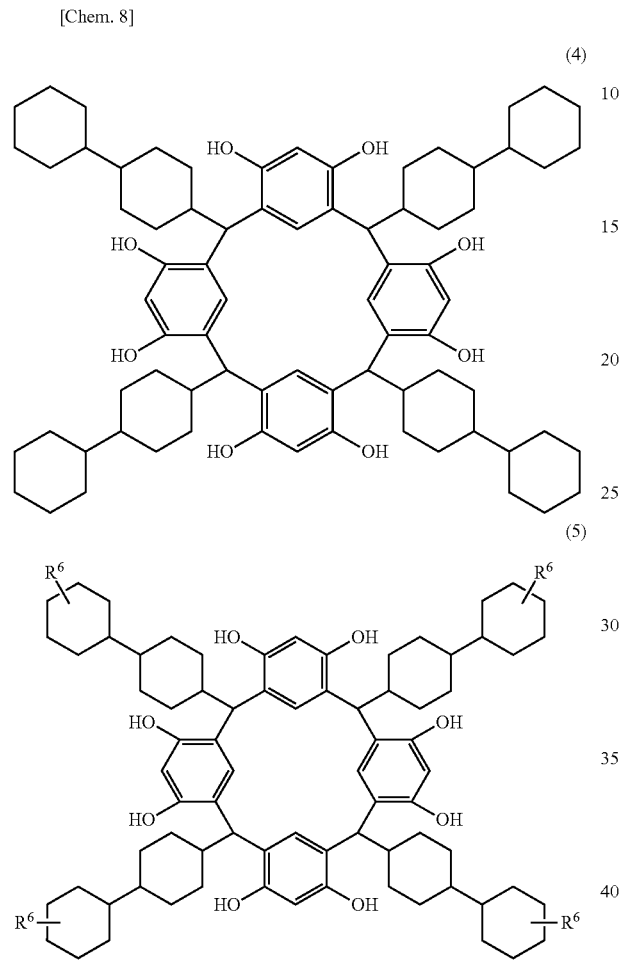

in the formula (5), $R^6$ is the same as described above.

16. A radiation sensitive composition according to the item 10, wherein the solid component comprises a cyclic compound/acid generator (C)/acid crosslinking agent (G)/acid-diffusion controller (E)/optional component (F) of 50-99.489/0.001-50/0.5-50/0.01-50/0-50% by weight based on the solid component.

17. A radiation sensitive composition according to the item 8, which is capable of forming an amorphous film with spin coating.

18. A radiation sensitive composition according to the item 17, wherein a dissolving speed of the amorphous film at 23° C. in an aqueous solution of 2.38% by weight of tetramethylammonium hydroxide is not less than 10 Å/sec.

19. A radiation sensitive composition according to the item 17, wherein a dissolving speed of the amorphous film after irradiated with KrF excimer laser, extreme ultraviolet ray, electron beams or X-ray or the amorphous film after heated at 20 to 250° C. in an aqueous solution of 2.38%) by weight of tetramethylammonium hydroxide is not more than 5 Å/sec.

20. A method of forming a resist pattern, which comprises a step of forming a resist film on a substrate using a radiation sensitive composition described in any one of the items 8 to 19, a step of exposing the resist film to radiation, and a step of developing the resist film to form a resist pattern.

21. A carbonyl compound (A1) represented by the following formula (6-1):

[Chem. 9]

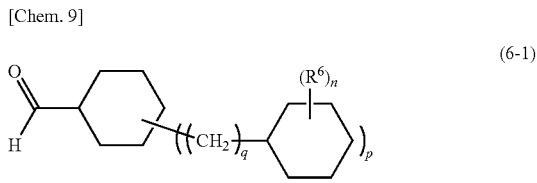

in the formula (6-1), $R^6$, n, p and q are the same as described above.

22. An acetal compound (A4) represented by the following formula (6-2):

[Chem. 10]

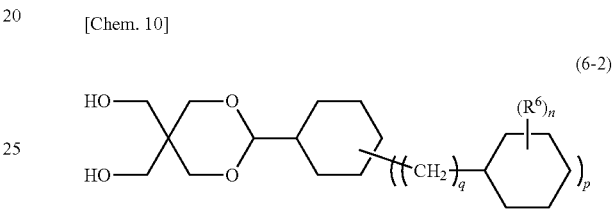

in the formula (6-2), $R^6$, n, p and q are the same as described above.

DETAILED DESCRIPTION OF THE PREFERRED EMBODIMENTS

According to the invention, it is capable of providing a cyclic compound being high in the solubility in safety solvents and high in the sensitivity and good in the shape of the resulting a resist pattern, a method of producing the same, a radiation sensitive composition comprising the same, and a method of forming a resist pattern using the radiation sensitive composition.

The invention will be described in more detail below.

[Cyclic Compound and Method of Producing the Same]

The invention relates to a cyclic compound useful as a resist material and a method of producing the same.

The cyclic compound of the invention is a cyclic compound represented by the following formula (1):

[Chem. 11]

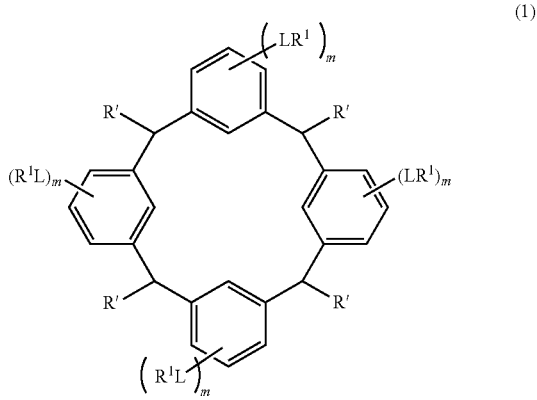

in the formula (1), L is independently a divalent group selected from the group consisting of a single bond, a linear or branched alkylene group having a carbon number of 1 to 20, a cycloalkylene group having a carbon number of 3 to 20, an arylene group having a carbon number of 6 to 24, —O—, —OC(=O)—, —OC(=O)O—, —N(R$^5$)—C(=O)—, —N(R$^5$)—C(=O)O—, —S—, —SO—, —SO$_2$— and any combination thereof; R$^1$ is independently a functional group selected from the group consisting of an alkyl group having a carbon number of 1 to 20, a cycloalkyl group having a carbon number of 3 to 20, an aryl group having a carbon number of 6 to 20, an alkoxyl group having a carbon number of 1 to 20, cyano group, nitro group, hydroxyl group, heterocyclic group, halogen, carboxyl group, an acyl group having a carbon number of 2 to 20, an alkylsilyl group having a carbon number of 1 to 20 and a derivative thereof, or a hydrogen atom, with the proviso that at least one of R$^1$ is a hydrogen atom; R' is independently a group represented by the following formula (1-2):

[Chem. 12]

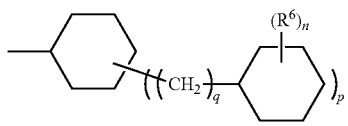

(1-2)

or a derivative thereof, R$^6$ is hydrogen or a functional group selected from the group consisting of an alkyl group having a carbon number of 1 to 12, a cycloalkyl group having a carbon number of 3 to 12, an aryl group having a carbon number of 6 to 12, an alkoxyl group having a carbon number of 1 to 12, cyano group, nitro group, heterocyclic group, halogen, carboxyl group, hydroxyl group and an alkylsilyl group having a carbon number of 1 to 12; m is an integer of 1 to 4; n is an integer of 0 to 5; p is an integer of 0 to 5; and q is an integer of 0 to 5.

The invention is preferable to be a cyclic compound represented by the following formula (2):

[Chem. 13]

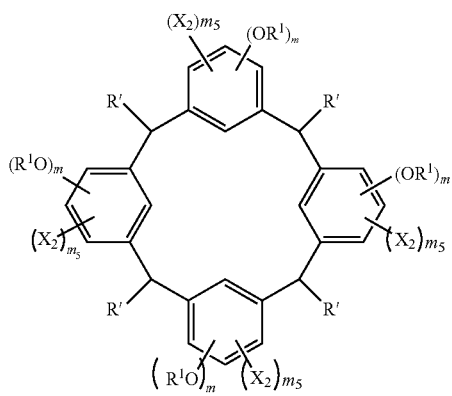

(2)

in the formula (2), R$^1$, R', p and m are the same as described above; X$_2$ is a hydrogen or halogen atom; m$_5$ is an integer of 0 to 3; and m+m$_5$=4.

The invention is preferable to be a cyclic compound represented by the following formula (3):

[Chem. 14]

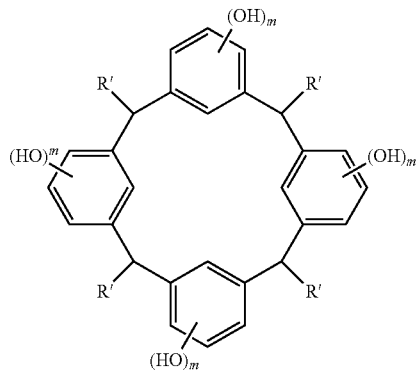

(3)

in the formula (3), R' and m are the same as described above.
R' is preferable to be a cyclic compound represented by the following formula (1-4):

[Chem. 15]

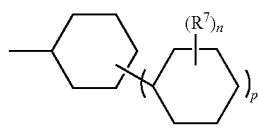

(1-4)

in the formula (1-4), R$^7$ is a functional group selected from the group consisting of an alkyl group having a carbon number of 1 to 12, a cycloalkyl group having a carbon number of 3 to 12, an aryl group having a carbon number of 6 to 12, an alkoxyl group having a carbon number of 1 to 12, cyano group, nitro group, heterocyclic group, halogen, carboxyl group, hydroxyl group, an alkylsilyl group having a carbon number of 1 to 12 and a derivative thereof; n is an integer of 0 to 5; and p is an integer of 0 to 5.

R' is preferable to be a cyclic compound represented by the following formula (1-5):

[Chem. 16]

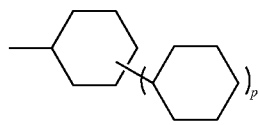

(1-5)

in the formula (1-5), p is an integer of 0 to 5.

The cyclic compound according to the invention is high in the heat resistance and excellent in the film-forming properties because of the amorphous nature, and has no sublimation and is also excellent in the alkali developability and resistance to etching, and is suitably used as a resist material, particularly a main component (base material) of the resist material.

In addition, from viewpoint of production, it is very excellent in the usefulness because it can be prepared in a high yield by a dehydration condensation reaction in the presence of a non-metallic catalyst such as hydrochloric acid while using various kinds of aldehydes including an industrially prepared aldehydes and phenols such as resorcinol, pyrogallol and the like as a starting material.

The cyclic compound is preferably a cyclic compound selected from the group consisting of compounds represented by the following formula (2-2):

[Chem. 17]

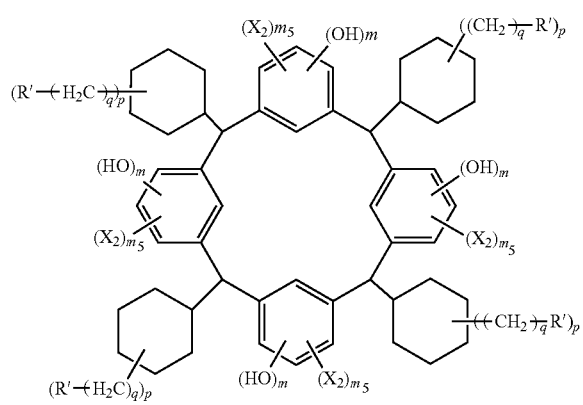

(2-2)

in the formula (2-2), R', $X_2$, p, q, m and $m_5$ are the same as described above.

The cyclic compound according to the invention is preferably a cyclic compound selected from the group consisting of compounds represented by the following formulae (4) and (5):

[Chem. 18]

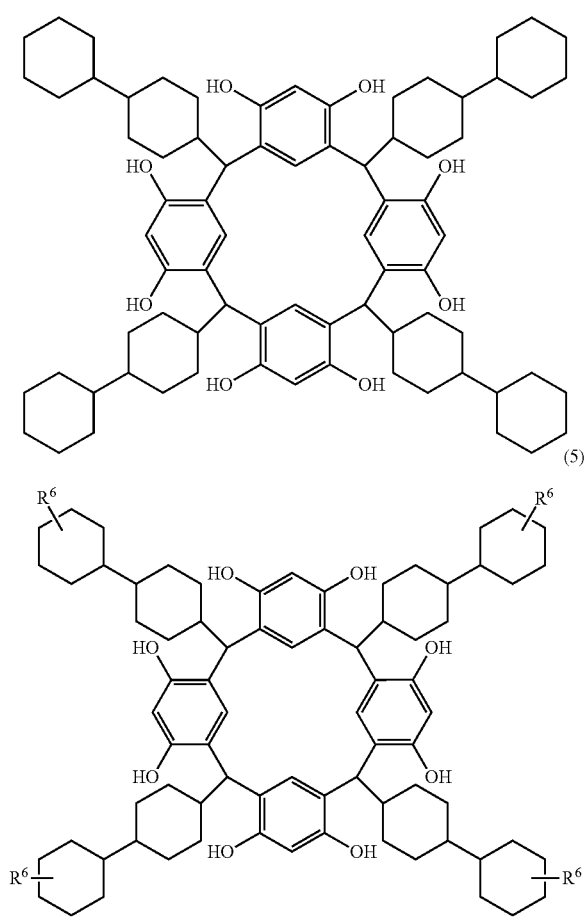

(4)

(5)

in the formula (5), $R^6$ is the same as described above.

The molecular weight of the cyclic compound represented by the formula (1) is 800 to 5000, preferably 800 to 2000, and more preferably 1000 to 2000. Within the above range, the resolution is improved while maintaining the film-forming properties required for the resist.

The cyclic compound of the invention may take a cis-isomer or a trans-isomer, but may be either one or a mixture of them. When it is used as a resist component of a radiation sensitive composition, the compound having either one of the cis-isomer and trans-isomer becomes a pure compound and is high in the uniformity of the component in the resulting resist film and is preferable. The method of providing the cyclic compound having only one of the cis-isomer and the trans-isomer may be carried out by known methods such as separation by column chromatography or preparative liquid chromatography, optimization of reaction solvent, reaction temperature and the like in the production, and so on.

The cyclic compound represented by the formula (1) is obtained by condensation reaction of one or more selected from the group consisting of compounds having a carbon number of 2 to 59 and 1 to 4 formyl groups (aldehydic compounds (A1A)) with one or more selected from the group consisting of phenolic compounds (A2).

More preferably, the cyclic compound represented by the formula (1) is obtained by condensation reaction of one or more selected from the group consisting of carbonyl compounds (A1) with one or more selected from the group consisting of phenolic compounds (A2).

An acetal compound (A4) of an aromatic carbonyl compound (A1) may be used instead of the carbonyl compound (A1).

The carbonyl compound (A1) is preferable to be a cyclohexylaldehyde represented by the following formula (6-1):

[Chem. 19]

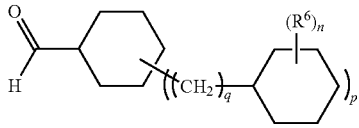

(6-1)

(in the formula (6-1), $R^6$, n, p and q are the same as described above), which includes, for example, 2-bicyclohexylaldehyde, 3-bicyclohexylaldehyde, 4-bicyclohexylaldehyde, 4-cyclohexylmethylcyclohexylaldehyde, 4-cyclohexylethylcyclohexylaldehyde, 4-cyclohexylpropylcyclohexylaldehyde, 4-cyclohexylbutylcyclohexylaldehyde, 4-cyclohexylpentylcyclohexylaldehyde, 4-cyclohexylhexylcyclohexylaldehyde, 4-cyclohexylheptylcyclohexylaldehyde, 4-cyclohexyloctylcyclohexylaldehyde, 4-cyclohexylnonylcyclohexylaldehyde, 4-cyclohexyldecanylcyclohexylaldehyde, 3-cyclohexylmethylcyclohexylaldehyde, 3-cyclohexylethylcyclohexylaldehyde, 3-cyclohexylpropylcyclohexylaldehyde, 3-cyclohexylbutylcyclohexylaldehyde, 3-cyclohexylpentylcyclohexylaldehyde, 3-cyclohexylhexylcyclohexylaldehyde, 3-cyclohexylheptylcyclohexylaldehyde, 3-cyclohexyloctylcyclohexylaldehyde, 3-cyclohexylnonylcyclohexylaldehyde, 3-cyclohexyldecanylcyclohexylaldehyde, 2-cyclohexylmethylcyclohexylaldehyde, 2-cyclohexylethylcyclohexylaldehyde, 2-cyclohexylpropylcyclohexylaldehyde, 2-cyclohexylbutylcyclohexylaldehyde, 2-cyclohexylpentylcyclohexylaldehyde, 2-cyclohexylhexylcyclohexylaldehyde, 2-cyclohexylheptylcyclohexylaldehyde, 2-cyclohexyloctylcyclohexylaldehyde, 2-cyclohexylnonylcyclohexylaldehyde, 2-cyclohexyldecanylcyclohexylaldehyde, 4-(4-methylcyclohexyl)cyclohexylaldehyde, 3-(4-methylcyclohexyl)cyclohexylaldehyde, 2-(4-methylcyclohexyl)cyclohexylaldehyde, 4-{(4-methylcyclohexyl)methyl}cyclohexylaldehyde, 3-{(4-methylcyclohexyl)methyl}cyclohexylaldehyde, 2-{(4-methylcyclohexyl)methyl}cyclohexylaldehyde, 4-{(3-methylcyclohexyl)ethyl}cyclohexylaldehyde, 3-{(3-methylcyclohexyl)ethyl}cyclohexylaldehyde, 2-{(3-methylcyclohexyl)ethyl}cyclohexylaldehyde, 4-{(3-methylcyclohexyl)propyl}cyclohexylaldehyde, 3-{(3-methylcyclohexyl)propyl}cyclohexylaldehyde, 2-{(3-methylcyclohexyl)propyl}cyclohexylaldehyde, 4-{(3-methylcyclohexyl)butyl}cyclohexylaldehyde, 3-{(3-methylcyclohexyl)butyl}cyclohexylaldehyde, 2-{(3-methylcyclohexyl)butyl}cyclohexylaldehyde, 4-{(3-methylcyclohexyl)pentyl}cyclohexylaldehyde, 3-{(3-methylcyclohexyl)pentyl}cyclohexylaldehyde, 2-{(3-methylcyclohexyl)pentyl}cyclohexylaldehyde, 4-{(3-methylcyclohexyl)hexyl}cyclohexylaldehyde, 3-{(3-methylcyclohexyl)hexyl}cyclohexylaldehyde, 2-{(3-methylcyclohexyl)hexyl}cyclohexylaldehyde, 4-{(3-methylcyclohexyl)heptyl}cyclohexylaldehyde, 3-{(3-methylcyclohexyl)heptyl}cyclohexylaldehyde, 2-{(3-methylcyclohexyl)heptyl}cyclohexylaldehyde, 4-{(3-methylcyclohexyl)octyl}cyclohexylaldehyde, 3-{(3-methylcyclohexyl)octyl}cyclohexylaldehyde, 2-{(3-methylcyclohexyl)octyl}cyclohexylaldehyde, 4-{(3-methylcyclohexyl)nonyl}cyclohexylaldehyde, 3-{(3-methylcyclohexyl)nonyl}cyclohexylaldehyde, 2-{(3-methylcyclohexyl)nonyl}cyclohexylaldehyde, 4-{(3-methylcyclohexyl)decanyl}cyclohexylaldehyde, 3-{(3-methylcyclohexyl)decanyl}cyclohexylaldehyde, 2-{(3-methylcyclohexyl)decanyl}cyclohexylaldehyde, 4-(4-ethylcyclohexyl)cyclohexylaldehyde, 3-(4-ethylcyclohexyl)cyclohexylaldehyde, 2-(4-ethylcyclohexyl)cyclohexylaldehyde, 4-{(4-ethylcyclohexyl)methyl}cyclohexylaldehyde, 3-{(4-ethylcyclohexyl)methyl}cyclohexylaldehyde, 2-{(4-ethylcyclohexyl)methyl}cyclohexylaldehyde, 4-{(3-ethylcyclohexyl)ethyl}cyclohexylaldehyde, 3-{(3-ethylcyclohexyl)ethyl}cyclohexylaldehyde, 2-{(3-ethylcyclohexyl)ethyl}cyclohexylaldehyde, 4-{(3-ethylcyclohexyl)propyl}cyclohexylaldehyde, 3-{(3-ethylcyclohexyl)propyl}cyclohexylaldehyde, 2-{(3-ethylcyclohexyl)propyl}cyclohexylaldehyde, 4-{(3-ethylcyclohexyl)butyl}cyclohexylaldehyde, 3-{(3-ethylcyclohexyl)butyl}cyclohexylaldehyde, 2-{(3-ethylcyclohexyl)butyl}cyclohexylaldehyde, 4-{(3-ethylcyclohexyl)pentyl}cyclohexylaldehyde, 3-{(3-ethylcyclohexyl)pentyl}cyclohexylaldehyde, 2-{(3-ethylcyclohexyl)pentyl}cyclohexylaldehyde, 4-{(3-ethylcyclohexyl)hexyl}cyclohexylaldehyde, 3-{(3-ethylcyclohexyl)hexyl}cyclohexylaldehyde, 2-{(3-ethylcyclohexyl)hexyl}cyclohexylaldehyde, 4-{(3-ethylcyclohexyl)heptyl}cyclohexylaldehyde, 3-{(3-ethylcyclohexyl)heptyl}cyclohexylaldehyde, 2-{(3-ethylcyclohexyl)heptyl}cyclohexylaldehyde, 4-{(3-ethylcyclohexyl)octyl}cyclohexylaldehyde, 3-{(3-ethylcyclohexyl)octyl}cyclohexylaldehyde, 2-{(3-ethylcyclohexyl)octyl}cyclohexylaldehyde, 4-{(3-ethylcyclohexyl)nonyl}cyclohexylaldehyde, 3-{(3-ethylcyclohexyl)nonyl}cyclohexylaldehyde, 2-{(3-ethylcyclohexyl)nonyl}cyclohexylaldehyde, 4-{(3-ethylcyclohexyl)decanyl}cyclohexylaldehyde, 3-{(3-ethylcyclohexyl)decanyl}cyclohexylaldehyde, 2-{(3-ethylcyclohexyl)decanyl}cyclohexylaldehyde, 4-(4-propylcyclohexyl)cyclohexylaldehyde, 3-(4-propylcyclohexyl)cyclohexylaldehyde, 2-(4-propylcyclohexyl)cyclohexylaldehyde, 4-{(4-propylcyclohexyl)methyl}cyclohexylaldehyde, 3-{(4-propylcyclohexyl)methyl}cyclohexylaldehyde, 2-{(4-propylcyclohexyl)methyl}cyclohexylaldehyde, 4-{(3-propylcyclohexyl)ethyl}cyclohexylaldehyde, 3-{(3-propylcyclohexyl)ethyl}cyclohexylaldehyde, 2-{(3-propylcyclohexyl)ethyl}cyclohexylaldehyde, 4-{(3-propylcyclohexyl)propyl}cyclohexylaldehyde, 3-{(3-propylcyclohexyl)propyl}cyclohexylaldehyde, 2-{(3-propylcyclohexyl)propyl}cyclohexylaldehyde, 4-{(3-propylcyclohexyl)butyl}cyclohexylaldehyde, 3-{(3-propylcyclohexyl)butyl}cyclohexylaldehyde, 2-{(3-propylcyclohexyl)butyl}cyclohexylaldehyde, 4-{(3-propylcyclohexyl)pentyl}cyclohexylaldehyde, 3-{(3-propylcyclohexyl)pentyl}cyclohexylaldehyde, 2-{(3-propylcyclohexyl)pentyl}cyclohexylaldehyde, 4-{(3-propylcyclohexyl)hexyl}cyclohexylaldehyde, 3-{(3-propylcyclohexyl)hexyl}cyclohexylaldehyde, 2-{(3-propylcyclohexyl)hexyl}cyclohexylaldehyde, 4-{(3-propylcyclohexyl)heptyl}cyclohexylaldehyde, 3-{(3-propylcyclohexyl)heptyl}cyclohexylaldehyde, 2-{(3-propylcyclohexyl)heptyl}cyclohexylaldehyde, 4-{(3-propylcyclohexyl)octyl}cyclohexylaldehyde, 3-{(3-propylcyclohexyl)octyl}cyclohexylaldehyde, 2-{(3-propylcyclohexyl)octyl}cyclohexylaldehyde, 4-{(3-propylcyclohexyl)nonyl}cyclohexylaldehyde, 3-{(3-propylcyclohexyl)nonyl}cyclohexylaldehyde, 2-{(3-propylcyclohexyl)nonyl}cyclohexylaldehyde, 4-{(3-propylcyclohexyl)decanyl}cyclohexylaldehyde, 3-{(3-propylcyclohexyl)decanyl}cyclohexylaldehyde, 2-{(3-propylcyclohexyl)decanyl}cyclohexylaldehyde, 4-(4-butylcyclohexyl)cyclohexylaldehyde, 3-(4-butylcyclohexyl)cyclohexylaldehyde, 2-(4-butylcyclohexyl)cyclohexylaldehyde, 4-{(4-butylcyclohexyl)methyl}cyclohexylaldehyde, 3-{(4-butylcyclohexyl)methyl}cyclohexylaldehyde, 2-{(4-butylcyclohexyl)methyl}cyclohexylaldehyde, 4-{(3-butylcyclohexyl)ethyl}cyclohexylaldehyde, 3-{(3-butylcyclohexyl)ethyl}cyclohexylaldehyde, 2-{(3-butylcyclohexyl)ethyl}cyclohexylaldehyde, 4-{(3-butylcyclohexyl)propyl}cyclohexylaldehyde, 3-{(3-butylcyclohexyl)propyl}cyclohexylaldehyde, 2-{(3-butylcyclohexyl)propyl}cyclohexylaldehyde, 4-{(3-butylcyclohexyl)butyl}cyclohexylaldehyde, 3-{(3-butylcyclohexyl)butyl}cyclohexylaldehyde, 2-{(3-butylcyclohexyl)butyl}cyclohexylaldehyde, 4-{(3-butylcyclohexyl)pentyl}cyclohexylaldehyde, 3-{(3-butylcyclohexyl)pentyl}cyclohexylaldehyde, 2-{(3-butylcyclohexyl)pentyl}cyclohexylaldehyde, 4-{(3-butylcyclohexyl)hexyl}cyclohexylaldehyde, 3-{(3-butylcyclohexyl)hexyl}cyclohexylaldehyde, 2-{(3-butylcyclohexyl)hexyl}cyclohexylaldehyde, 4-{(3-butylcyclohexyl)heptyl}cyclohexylaldehyde, 3-{(3-butylcyclohexyl)heptyl}cyclohexylaldehyde, 2-{(3-butylcyclohexyl)heptyl}cyclohexylaldehyde, 4-{(3-butylcyclohexyl)octyl}cyclohexylaldehyde, 3-{(3-butylcyclohexyl)octyl}cyclohexylaldehyde, 2-{(3-butylcyclohexyl)octyl}cyclohexylaldehyde, 4-{(3-butylcyclohexyl)nonyl}cyclohexylaldehyde, 3-{(3-butylcyclohexyl)nonyl}cyclohexylaldehyde, 2-{(3-butylcyclohexyl)nonyl}cyclohexylaldehyde, 4-{(3-butylcyclohexyl)decanyl}cyclohexylaldehyde, 3-{(3-butylcyclohexyl)decanyl}cyclohexylaldehyde, 2-{(3-butylcyclohexyl)decanyl}cyclohexylaldehyde, 4-(2,4-dimethylcyclohexyl)cyclohexylaldehyde, 3-(2,4-dimethylcyclohexyl)

cyclohexylaldehyde, 2-(2,4-dimethylcyclohexyl)cyclohexylaldehyde, 4-{(2,4-dimethylcyclohexyl)methyl}cyclohexylaldehyde, 3-{(2,4-dimethylcyclohexyl)methyl}cyclohexylaldehyde, 2-{(2,4-dimethylcyclohexyl)methyl}cyclohexylaldehyde, 4-{(2,4-dimethylcyclohexyl)ethyl}cyclohexylaldehyde, 3-{(2,4-dimethylcyclohexyl)ethyl}cyclohexylaldehyde, 2-{(2,4-dimethylcyclohexyl)ethyl}cyclohexylaldehyde, 4-{(2,4-dimethylcyclohexyl)propyl}cyclohexylaldehyde, 3-{(2,4-dimethylcyclohexyl)propyl}cyclohexylaldehyde, 2-{(2,4-dimethylcyclohexyl)propyl}cyclohexylaldehyde, 4-{(2,4-dimethylcyclohexyl)butyl}cyclohexylaldehyde, 3-{(2,4-dimethylcyclohexyl)butyl}cyclohexylaldehyde, 2-{(2,4-dimethylcyclohexyl)butyl}cyclohexylaldehyde, 4-{(2,4-dimethylcyclohexyl)pentyl}cyclohexylaldehyde, 3-{(2,4-dimethylcyclohexyl)pentyl}cyclohexylaldehyde, 2-{(2,4-dimethylcyclohexyl)pentyl}cyclohexylaldehyde, 4-{(2,4-dimethylcyclohexyl)hexyl}cyclohexylaldehyde, 3-{(2,4-dimethylcyclohexyl)hexyl}cyclohexylaldehyde, 2-{(2,4-dimethylcyclohexyl)hexyl}cyclohexylaldehyde, 4-{(2,4-dimethylcyclohexyl)heptyl}cyclohexylaldehyde, 3-{(2,4-dimethylcyclohexyl)heptyl}cyclohexylaldehyde, 2-{(2,4-dimethylcyclohexyl)heptyl}cyclohexylaldehyde, 4-{(2,4-dimethylcyclohexyl)octyl}cyclohexylaldehyde, 3-{(2,4-dimethylcyclohexyl)octyl}cyclohexylaldehyde, 2-{(2,4-dimethylcyclohexyl)octyl}cyclohexylaldehyde, 4-{(2,4-dimethylcyclohexyl)nonyl}cyclohexylaldehyde, 3-{(2,4-dimethylcyclohexyl)nonyl}cyclohexylaldehyde, 2-{(2,4-dimethylcyclohexyl)nonyl}cyclohexylaldehyde, 4-{(2,4-dimethylcyclohexyl)decanyl}cyclohexylaldehyde, 3-{(2,4-dimethylcyclohexyl)decanyl}cyclohexylaldehyde, 2-{(2,4-dimethylcyclohexyl)decanyl}cyclohexylaldehyde, 4-(3,4-dimethylcyclohexyl)cyclohexylaldehyde, 3-(3,4-dimethylcyclohexyl)cyclohexylaldehyde, 2-(3,4-dimethylcyclohexyl)cyclohexylaldehyde, 4-{(3,4-dimethylcyclohexyl)methyl}cyclohexylaldehyde, 3-{(3,4-dimethylcyclohexyl)methyl}cyclohexylaldehyde, 2-{(3,4-dimethylcyclohexyl)methyl}cyclohexylaldehyde, 4-{(3,4-dimethylcyclohexyl)ethyl}cyclohexylaldehyde, 3-{(3,4-dimethylcyclohexyl)ethyl}cyclohexylaldehyde, 2-{(3,4-dimethylcyclohexyl)ethyl}cyclohexylaldehyde, 4-{(3,4-dimethylcyclohexyl)propyl}cyclohexylaldehyde, 3-{(3,4-dimethylcyclohexyl)propyl}cyclohexylaldehyde, 2-{(3,4-dimethylcyclohexyl)propyl}cyclohexylaldehyde, 4-{(3,4-dimethylcyclohexyl)butyl}cyclohexylaldehyde, 3-{(3,4-dimethylcyclohexyl)butyl}cyclohexylaldehyde, 2-{(3,4-dimethylcyclohexyl)butyl}cyclohexylaldehyde, 4-{(3,4-dimethylcyclohexyl)pentyl}cyclohexylaldehyde, 3-{(3,4-dimethylcyclohexyl)pentyl}cyclohexylaldehyde, 2-{(3,4-dimethylcyclohexyl)pentyl}cyclohexylaldehyde, 4-{(3,4-dimethylcyclohexyl)hexyl}cyclohexylaldehyde, 3-{(3,4-dimethylcyclohexyl)hexyl}cyclohexylaldehyde, 2-{(3,4-dimethylcyclohexyl)hexyl}cyclohexylaldehyde, 4-{(3,4-dimethylcyclohexyl)heptyl}cyclohexylaldehyde, 3-{(3,4-dimethylcyclohexyl)heptyl}cyclohexylaldehyde, 2-{(3,4-dimethylcyclohexyl)heptyl}cyclohexylaldehyde, 4-{(3,4-dimethylcyclohexyl)octyl}cyclohexylaldehyde, 3-{(3,4-dimethylcyclohexyl)octyl}cyclohexylaldehyde, 2-{(3,4-dimethylcyclohexyl)octyl}cyclohexylaldehyde, 4-{(3,4-dimethylcyclohexyl)nonyl}cyclohexylaldehyde, 3-{(3,4-dimethylcyclohexyl)nonyl}cyclohexylaldehyde, 2-{(3,4-dimethylcyclohexyl)nonyl}cyclohexylaldehyde, 4-{(3,4-dimethylcyclohexyl)decanyl}cyclohexylaldehyde, 3-{(3,4-dimethylcyclohexyl)decanyl}cyclohexylaldehyde, 2-{(3,4-dimethylcyclohexyl)decanyl}cyclohexylaldehyde, 4-(2,3-dimethylcyclohexyl)cyclohexylaldehyde, 3-(2,3-dimethylcyclohexyl)cyclohexylaldehyde, 2-(2,3-dimethylcyclohexyl)cyclohexylaldehyde, 4-{(2,3-dimethylcyclohexyl)methyl}cyclohexylaldehyde, 3-{(2,3-dimethylcyclohexyl)methyl}cyclohexylaldehyde, 2-{(2,3-dimethylcyclohexyl)methyl}cyclohexylaldehyde, 4-{(2,3-dimethylcyclohexyl)ethyl}cyclohexylaldehyde, 3-{(2,3-dimethylcyclohexyl)ethyl}cyclohexylaldehyde, 2-{(2,3-dimethylcyclohexyl)ethyl}cyclohexylaldehyde, 4-{(2,3-dimethylcyclohexyl)propyl}cyclohexylaldehyde, 3-{(2,3-dimethylcyclohexyl)propyl}cyclohexylaldehyde, 2-{(2,3-dimethylcyclohexyl)propyl}cyclohexylaldehyde, 4-{(2,3-dimethylcyclohexyl)butyl}cyclohexylaldehyde, 3-{(2,3-dimethylcyclohexyl)butyl}cyclohexylaldehyde, 2-{(2,3-dimethylcyclohexyl)butyl}cyclohexylaldehyde, 4-{(2,3-dimethylcyclohexyl)pentyl}cyclohexylaldehyde, 3-{(2,3-dimethylcyclohexyl)pentyl}cyclohexylaldehyde, 2-{(2,3-dimethylcyclohexyl)pentyl}cyclohexylaldehyde, 4-{(2,3-dimethylcyclohexyl)hexyl}cyclohexylaldehyde, 3-{(2,3-dimethylcyclohexyl)hexyl}cyclohexylaldehyde, 2-{(2,3-dimethylcyclohexyl)hexyl}cyclohexylaldehyde, 4-{(2,3-dimethylcyclohexyl)heptyl}cyclohexylaldehyde, 3-{(2,3-dimethylcyclohexyl)heptyl}cyclohexylaldehyde, 2-{(2,3-dimethylcyclohexyl)heptyl}cyclohexylaldehyde, 4-{(2,3-dimethylcyclohexyl)octyl}cyclohexylaldehyde, 3-{(2,3-dimethylcyclohexyl)octyl}cyclohexylaldehyde, 2-{(2,3-dimethylcyclohexyl)octyl}cyclohexylaldehyde, 4-{(2,3-dimethylcyclohexyl)nonyl}cyclohexylaldehyde, 3-{(2,3-dimethylcyclohexyl)nonyl}cyclohexylaldehyde, 2-{(2,3-dimethylcyclohexyl)nonyl}cyclohexylaldehyde, 4-{(2,3-dimethylcyclohexyl)decanyl}cyclohexylaldehyde, 3-{(2,3-dimethylcyclohexyl)decanyl}cyclohexylaldehyde, 2-{(2,3-dimethylcyclohexyl)decanyl}cyclohexylaldehyde, 4-(3,5-dimethylcyclohexyl)cyclohexylaldehyde, 3-(3,5-dimethylcyclohexyl)cyclohexylaldehyde, 2-(3,5-dimethylcyclohexyl)cyclohexylaldehyde, 4-{(3,5-dimethylcyclohexyl)methyl}cyclohexylaldehyde, 3-{(3,5-dimethylcyclohexyl)methyl}cyclohexylaldehyde, 2-{(3,5-dimethylcyclohexyl)methyl}cyclohexylaldehyde, 4-{(3,5-dimethylcyclohexyl)ethyl}cyclohexylaldehyde, 3-{(3,5-dimethylcyclohexyl)ethyl}cyclohexylaldehyde, 2-{(3,5-dimethylcyclohexyl)ethyl}cyclohexylaldehyde, 4-{(3,5-dimethylcyclohexyl)propyl}cyclohexylaldehyde, 3-{(3,5-dimethylcyclohexyl)propyl}cyclohexylaldehyde, 2-{(3,5-dimethylcyclohexyl)propyl}cyclohexylaldehyde, 4-{(3,5-dimethylcyclohexyl)butyl}cyclohexylaldehyde, 3-{(3,5-dimethylcyclohexyl)butyl}cyclohexylaldehyde, 2-{(3,5-dimethylcyclohexyl)butyl}cyclohexylaldehyde, 4-{(3,5-dimethylcyclohexyl)pentyl}cyclohexylaldehyde, 3-{(3,5-dimethylcyclohexyl)pentyl}cyclohexylaldehyde, 2-{(3,5-dimethylcyclohexyl)pentyl}cyclohexylaldehyde, 4-{(3,5-dimethylcyclohexyl)hexyl}cyclohexylaldehyde, 3-{(3,5-dimethylcyclohexyl)hexyl}cyclohexylaldehyde, 2-{(3,5-dimethylcyclohexyl)hexyl}cyclohexylaldehyde, 4-{(3,5-dimethylcyclohexyl)heptyl}cyclohexylaldehyde, 3-{(3,5-dimethylcyclohexyl)heptyl}cyclohexylaldehyde, 2-{(3,5-dimethylcyclohexyl)heptyl}cyclohexylaldehyde, 4-{(3,5-dimethylcyclohexyl)octyl}cyclohexylaldehyde, 3-{(3,5-dimethylcyclohexyl)octyl}cyclohexylaldehyde, 2-{(3,5-dimethylcyclohexyl)octyl}cyclohexylaldehyde, 4-{(3,5-dimethylcyclohexyl)nonyl}cyclohexylaldehyde, 3-{(3,5-dimethylcyclohexyl)nonyl}cyclohexylaldehyde, 2-{(3,5-dimethylcyclohexyl)nonyl}cyclohexylaldehyde, 4-{(3,5-dimethylcyclohexyl)decanyl}cyclohexylaldehyde, 3-{(3,5-dimethylcyclohexyl)decanyl}cyclohexylaldehyde, 2-{(3,5-dimethylcyclohexyl)decanyl}cyclohexylaldehyde, 4-(2,6-dimethylcyclohexyl)cyclohexylaldehyde, 3-(2,6-dimethylcyclohexyl)cyclohexylaldehyde, 2-(2,6-dimethylcyclohexyl)cyclohexylaldehyde, 4-{(2,6-dimethylcyclohexyl)

methyl}cyclohexylaldehyde, 3-{(2,6-dimethylcyclohexyl)methyl}cyclohexylaldehyde, 2-{(2,6-dimethylcyclohexyl)methyl}cyclohexylaldehyde, 4-{(2,6-dimethylcyclohexyl)ethyl}cyclohexylaldehyde, 3-{(2,6-dimethylcyclohexyl)ethyl}cyclohexylaldehyde, 2-{(2,6-dimethylcyclohexyl)ethyl}cyclohexylaldehyde, 4-{(2,6-dimethylcyclohexyl)propyl}cyclohexylaldehyde, 3-{(2,6-dimethylcyclohexyl)propyl}cyclohexylaldehyde, 2-{(2,6-dimethylcyclohexyl)propyl}cyclohexylaldehyde, 4-{(2,6-dimethylcyclohexyl)butyl}cyclohexylaldehyde, 3-{(2,6-dimethylcyclohexyl)butyl}cyclohexylaldehyde, 2-{(2,6-dimethylcyclohexyl)butyl}cyclohexylaldehyde, 4-{(2,6-dimethylcyclohexyl)pentyl}cyclohexylaldehyde, 3-{(2,6-dimethylcyclohexyl)pentyl}cyclohexylaldehyde, 2-{(2,6-dimethylcyclohexyl)pentyl}cyclohexylaldehyde, 4-{(2,6-dimethylcyclohexyl)hexyl}cyclohexylaldehyde, 3-{(2,6-dimethylcyclohexyl)hexyl}cyclohexylaldehyde, 2-{(2,6-dimethylcyclohexyl)hexyl}cyclohexylaldehyde, 4-{(2,6-dimethylcyclohexyl)heptyl}cyclohexylaldehyde, 3-{(2,6-dimethylcyclohexyl)heptyl}cyclohexylaldehyde, 2-{(2,6-dimethylcyclohexyl)heptyl}cyclohexylaldehyde, 4-{(2,6-dimethylcyclohexyl)octyl}cyclohexylaldehyde, 3-{(2,6-dimethylcyclohexyl)octyl}cyclohexylaldehyde, 2-{(2,6-dimethylcyclohexyl)octyl}cyclohexylaldehyde, 4-{(2,6-dimethylcyclohexyl)nonyl}cyclohexylaldehyde, 3-{(2,6-dimethylcyclohexyl)nonyl}cyclohexylaldehyde, 2-{(2,6-dimethylcyclohexyl)nonyl}cyclohexylaldehyde, 4-{(2,6-dimethylcyclohexyl)decanyl}cyclohexylaldehyde, 3-{(2,6-dimethylcyclohexyl)decanyl}cyclohexylaldehyde, 2-{(2,6-dimethylcyclohexyl)decanyl}cyclohexylaldehyde and so on. 2-bicyclohexylaldehyde, 3-bicyclohexylaldehyde and 4-bicyclohexylaldehyde are preferable, and 4-bicyclohexylaldehyde is more preferable. The carbonyl compound (A1) may have a linear or branched alkyl group having a carbon number of 1 to 4, cyano group, hydroxyl group, a halogen atom and so on within a range not damaging the effect of the invention. The carbonyl compounds (A1) may be used alone or in a combination of two or more.

The acetal compound (A4) of the carbonyl compound is a compound having a carbonyl group protected with an acetal group, and is preferably pentaerythritol acetal of cyclohexylaldehyde represented by the following formula (6-2):

[Chem. 20]

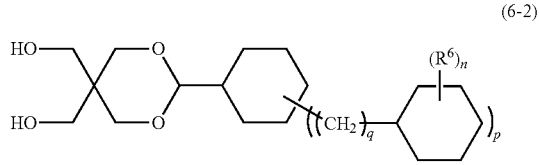

(6-2)

(in the formula (6-2), $R^6$, n, p and q are the same as described above).

As the pentaerythritol acetal are mentioned, for example, 2-bicyclohexylaldehyde pentaerythritol acetal, 3-bicyclohexylaldehyde pentaerythritol acetal, 4-bicyclohexylaldehyde pentaerythritol acetal, 4-cyclohexylmethylcyclohexylaldehyde pentaerythritol acetal, 4-cyclohexylethylcyclohexylaldehyde pentaerythritol acetal, 4-cyclohexylpropylcyclohexylaldehyde pentaerythritol acetal, 4-cyclohexylbuthylcyclohexylaldehyde pentaerythritol acetal, 4-cyclohexylpenthylcyclohexylaldehyde pentaerythritol acetal, 4-cyclohexylhexylcyclohexylaldehyde pentaerythritol acetal, 4-cyclohexylhepthylcyclohexylaldehyde pentaerythritol acetal, 4-cyclohexyoethylcyclohexylaldehyde pentaerythritol acetal, 4-cyclohexylnonylcyclohexylaldehyde pentaerythritol acetal, 4-cyclohexyldecanylcyclohexylaldehyde pentaerythritol acetal, 3-cyclohexylmethylcyclohexylaldehyde pentaerythritol acetal, 3-cyclohexylethylcyclohexylaldehyde pentaerythritol acetal, 3-cyclohexylpropylcyclohexylaldehyde pentaerythritol acetal, 3-cyclohexylbuthylcyclohexylaldehyde pentaerythritol acetal, 3-cyclohexylpentylcyclohexylaldehyde pentaerythritol acetal, 3-cyclohexylhexylcyclohexylaldehyde pentaerythritol acetal, 3-cyclohexylheptylcyclohexylaldehyde pentaerythritol acetal, 3-cyclohexyloctylcyclohexylaldehyde pentaerythritol acetal, 3-cyclohexylnonylcyclohexylaldehyde pentaerythritol acetal, 3-cyclohexyldecanylcyclohexylaldehyde pentaerythritol acetal, 2-cyclohexylmethylcyclohexylaldehyde pentaerythritol acetal, 2-cyclohexylethylcyclohexylaldehyde pentaerythritol acetal, 2-cyclohexylpropylcyclohexylaldehyde pentaerythritol acetal, 2-cyclohexylbutylcyclohexylaldehyde pentaerythritol acetal, 2-cyclohexylpentylcyclohexylaldehyde pentaerythritol acetal, 2-cyclohexylhexylcyclohexylaldehyde pentaerythritol acetal, 2-cyclohexylheptylcyclohexylaldehyde pentaerythritol acetal, 2-cyclohexyloctylcyclohexylaldehyde pentaerythritol acetal, 2-cyclohexylnonylcyclohexylaldehyde pentaerythritol acetal, 2-cyclohexyldecanylcyclohexylaldehyde pentaerythritol acetal, 4-(4-methylcyclohexyl)cyclohexylaldehyde pentaerythritol acetal, 3-(4-methylcyclohexyl)cyclohexylaldehyde pentaerythritol acetal, 2-(4-methylcyclohexyl)cyclohexylaldehyde pentaerythritol acetal, 4-{(4-methylcyclohexyl)methyl}cyclohexylaldehyde pentaerythritol acetal, 3-{(4-methylcyclohexyl)methyl}cyclohexylaldehyde pentaerythritol acetal, 2-{(4-methylcyclohexyl)methyl}cyclohexylaldehyde pentaerythritol acetal, 4-{(3-methylcyclohexyl)ethyl}cyclohexylaldehyde pentaerythritol acetal, 3-{(3-methylcyclohexyl)ethyl}cyclohexylaldehyde pentaerythritol acetal, 2-{(3-methylcyclohexyl)ethyl}cyclohexylaldehyde pentaerythritol acetal, 4-{(3-methylcyclohexyl)propyl}cyclohexylaldehyde pentaerythritol acetal, 3-{(3-methylcyclohexyl)propyl}cyclohexylaldehyde pentaerythritol acetal, 2-{(3-methylcyclohexyl)propyl}cyclohexylaldehyde pentaerythritol acetal, 4-{(3-methylcyclohexyl)butyl}cyclohexylaldehyde pentaerythritol acetal, 3-{(3-methylcyclohexyl)butyl}cyclohexylaldehyde pentaerythritol acetal, 2-{(3-methylcyclohexyl)butyl}cyclohexylaldehyde pentaerythritol acetal, 4-{(3-methylcyclohexyl)pentyl}cyclohexylaldehyde pentaerythritol acetal, 3-{(3-methylcyclohexyl)pentyl}cyclohexylaldehyde pentaerythritol acetal, 2-{(3-methylcyclohexyl)pentyl}cyclohexylaldehyde pentaerythritol acetal, 4-{(3-methylcyclohexyl)hexyl}cyclohexylaldehyde pentaerythritol acetal, 3-{(3-methylcyclohexyl)hexyl}cyclohexylaldehyde pentaerythritol acetal, 2-{(3-methylcyclohexyl)hexyl}cyclohexylaldehyde pentaerythritol acetal, 4-{(3-methylcyclohexyl)heptyl}cyclohexylaldehyde pentaerythritol acetal, 3-{(3-methylcyclohexyl)heptyl}cyclohexylaldehyde pentaerythritol acetal, 2-{(3-methylcyclohexyl)heptyl}cyclohexylaldehyde pentaerythritol acetal, 4-{(3-methylcyclohexyl)octyl}cyclohexylaldehyde pentaerythritol acetal, 3-{(3-methylcyclohexyl)octyl}cyclohexylaldehyde pentaerythritol acetal, 2-{(3-methylcyclohexyl)octyl}cyclohexylaldehyde pentaerythritol acetal, 4-{(3-methylcyclohexyl)nonyl}cyclohexylaldehyde pentaerythritol acetal, 3-{(3-methylcyclohexyl)nonyl}cyclohexylaldehyde pentaerythritol acetal, 2-{(3-methylcyclohexyl)nonyl}cyclohexylaldehyde pentaerythritol acetal, 4-{(3-methylcyclohexyl)

decanyl}cyclohexylaldehyde pentaerythritol acetal, 3-{(3-methylcyclohexyl)decanyl}cyclohexylaldehyde pentaerythritol acetal, 2-{(3-methylcyclohexyl)decanyl}cyclohexylaldehyde pentaerythritol acetal, 4-(4-ethylcyclohexyl)cyclohexylaldehyde pentaerythritol acetal, 3-(4-ethylcyclohexyl)cyclohexylaldehyde pentaerythritol acetal, 2-(4-ethylcyclohexyl)cyclohexylaldehyde pentaerythritol acetal, 4-{(4-ethylcyclohexyl)methyl}cyclohexylaldehyde pentaerythritol acetal, 3-{(4-ethylcyclohexyl)methyl}cyclohexylaldehyde pentaerythritol acetal, 2-{(4-ethylcyclohexyl)methyl}cyclohexylaldehyde pentaerythritol acetal, 4-{(3-ethylcyclohexyl)ethyl}cyclohexylaldehyde pentaerythritol acetal, 3-{(3-ethylcyclohexyl)ethyl}cyclohexylaldehyde pentaerythritol acetal, 2-{(3-ethylcyclohexyl)ethyl}cyclohexylaldehyde pentaerythritol acetal, 4-{(3-ethylcyclohexyl)propyl}cyclohexylaldehyde pentaerythritol acetal, 3-{(3-ethylcyclohexyl)propyl}cyclohexylaldehyde pentaerythritol acetal, 2-{(3-ethylcyclohexyl)propyl}cyclohexylaldehyde pentaerythritol acetal, 4-{(3-ethylcyclohexyl)butyl}cyclohexylaldehyde pentaerythritol acetal, 3-{(3-ethylcyclohexyl)butyl}cyclohexylaldehyde pentaerythritol acetal, 2-{(3-ethylcyclohexyl)butyl}cyclohexylaldehyde pentaerythritol acetal, 4-{(3-ethylcyclohexyl)pentyl}cyclohexylaldehyde pentaerythritol acetal, 3-{(3-ethylcyclohexyl)pentyl}cyclohexylaldehyde pentaerythritol acetal, 2-{(3-ethylcyclohexyl)pentyl}cyclohexylaldehyde pentaerythritol acetal, 4-{(3-ethylcyclohexyl)hexyl}cyclohexylaldehyde pentaerythritol acetal, 3-{(3-ethylcyclohexyl)hexyl}cyclohexylaldehyde pentaerythritol acetal, 2-{(3-ethylcyclohexyl)hexyl}cyclohexylaldehyde pentaerythritol acetal, 4-{(3-ethylcyclohexyl)heptyl}cyclohexylaldehyde pentaerythritol acetal, 3-{(3-ethylcyclohexyl)heptyl}cyclohexylaldehyde pentaerythritol acetal, 2-{(3-ethylcyclohexyl)heptyl}cyclohexylaldehyde pentaerythritol acetal, 4-{(3-ethylcyclohexyl)octyl}cyclohexylaldehyde pentaerythritol acetal, 3-{(3-ethylcyclohexyl)octyl}cyclohexylaldehyde pentaerythritol acetal, 2-{(3-ethylcyclohexyl)octyl}cyclohexylaldehyde pentaerythritol acetal, 4-{(3-ethylcyclohexyl)nonyl}cyclohexylaldehyde pentaerythritol acetal, 3-{(3-ethylcyclohexyl)nonyl}cyclohexylaldehyde pentaerythritol acetal, 2-{(3-ethylcyclohexyl)nonyl}cyclohexylaldehyde pentaerythritol acetal, 4-{(3-ethylcyclohexyl)decanyl}cyclohexylaldehyde pentaerythritol acetal, 3-{(3-ethylcyclohexyl)decanyl}cyclohexylaldehyde pentaerythritol acetal, 2-{(3-ethylcyclohexyl)decanyl}cyclohexylaldehyde pentaerythritol acetal, 4-(4-propylcyclohexyl)cyclohexylaldehyde pentaerythritol acetal, 3-(4-propylcyclohexyl)cyclohexylaldehyde pentaerythritol acetal, 2-(4-propylcyclohexyl)cyclohexylaldehyde pentaerythritol acetal, 4-{(4-propylcyclohexyl)methyl}cyclohexylaldehyde pentaerythritol acetal, 3-{(4-propylcyclohexyl)methyl}cyclohexylaldehyde pentaerythritol acetal, 2-{(4-propylcyclohexyl)methyl}cyclohexylaldehyde pentaerythritol acetal, 4-{(3-propylcyclohexyl)ethyl}cyclohexylaldehyde pentaerythritol acetal, 3-{(3-propylcyclohexyl)ethyl}cyclohexylaldehyde pentaerythritol acetal, 2-{(3-propylcyclohexyl)ethyl}cyclohexylaldehyde pentaerythritol acetal, 4-{(3-propylcyclohexyl)propyl}cyclohexylaldehyde pentaerythritol acetal, 3-{(3-propylcyclohexyl)propyl}cyclohexylaldehyde pentaerythritol acetal, 2-{(3-propylcyclohexyl)propyl}cyclohexylaldehyde pentaerythritol acetal, 4-{(3-propylcyclohexyl)butyl}cyclohexylaldehyde pentaerythritol acetal, 3-{(3-propylcyclohexyl)butyl}cyclohexylaldehyde pentaerythritol acetal, 2-{(3-propylcyclohexyl)butyl}cyclohexylaldehyde pentaerythritol acetal, 4-{(3-propylcyclohexyl)pentyl}cyclohexylaldehyde pentaerythritol acetal, 3-{(3-propylcyclohexyl)pentyl}cyclohexylaldehyde pentaerythritol acetal, 2-{(3-propylcyclohexyl)pentyl}cyclohexylaldehyde pentaerythritol acetal, 4-{(3-propylcyclohexyl)hexyl}cyclohexylaldehyde pentaerythritol acetal, 3-{(3-propylcyclohexyl)hexyl}cyclohexylaldehyde pentaerythritol acetal, 2-{(3-propylcyclohexyl)hexyl}cyclohexylaldehyde pentaerythritol acetal, 4-{(3-propylcyclohexyl)heptyl}cyclohexylaldehyde pentaerythritol acetal, 3-{(3-propylcyclohexyl)heptyl}cyclohexylaldehyde pentaerythritol acetal, 2-{(3-propylcyclohexyl)heptyl}cyclohexylaldehyde pentaerythritol acetal, 4-{(3-propylcyclohexyl)octyl}cyclohexylaldehyde pentaerythritol acetal, 3-{(3-propylcyclohexyl)octyl}cyclohexylaldehyde pentaerythritol acetal, 2-{(3-propylcyclohexyl)octyl}cyclohexylaldehyde pentaerythritol acetal, 4-{(3-propylcyclohexyl)nonyl}cyclohexylaldehyde pentaerythritol acetal, 3-{(3-propylcyclohexyl)nonyl}cyclohexylaldehyde pentaerythritol acetal, 2-{(3-propylcyclohexyl)nonyl}cyclohexylaldehyde pentaerythritol acetal, 4-{(3-propylcyclohexyl)decanyl}cyclohexylaldehyde pentaerythritol acetal, 3-{(3-propylcyclohexyl)decanyl}cyclohexylaldehyde pentaerythritol acetal, 2-{(3-propylcyclohexyl)decanyl}cyclohexylaldehyde pentaerythritol acetal, 4-(4-butylcyclohexyl)cyclohexylaldehyde pentaerythritol acetal, 3-(4-butylcyclohexyl)cyclohexylaldehyde pentaerythritol acetal, 2-(4-butylcyclohexyl)cyclohexylaldehyde pentaerythritol acetal, 4-{(4-butylcyclohexyl)methyl}cyclohexylaldehyde pentaerythritol acetal, 3-{(4-butylcyclohexyl)methyl}cyclohexylaldehyde pentaerythritol acetal, 2-{(4-butylcyclohexyl)methyl}cyclohexylaldehyde pentaerythritol acetal, 4-{(3-butylcyclohexyl)ethyl}cyclohexylaldehyde pentaerythritol acetal, 3-{(3-butylcyclohexyl)ethyl}cyclohexylaldehyde pentaerythritol acetal, 2-{(3-butylcyclohexyl)ethyl}cyclohexylaldehyde pentaerythritol acetal, 4-{(3-butylcyclohexyl)propyl}cyclohexylaldehyde pentaerythritol acetal, 3-{(3-butylcyclohexyl)propyl}cyclohexylaldehyde pentaerythritol acetal, 2-{(3-butylcyclohexyl)propyl}cyclohexylaldehyde pentaerythritol acetal, 4-{(3-butylcyclohexyl)butyl}cyclohexylaldehyde pentaerythritol acetal, 3-{(3-butylcyclohexyl)butyl}cyclohexylaldehyde pentaerythritol acetal, 2-{(3-butylcyclohexyl)butyl}cyclohexylaldehyde pentaerythritol acetal, 4-{(3-butylcyclohexyl)pentyl}cyclohexylaldehyde pentaerythritol acetal, 3-{(3-butylcyclohexyl)pentyl}cyclohexylaldehyde pentaerythritol acetal, 2-{(3-butylcyclohexyl)pentyl}cyclohexylaldehyde pentaerythritol acetal, 4-{(3-butylcyclohexyl)hexyl}cyclohexylaldehyde pentaerythritol acetal, 3-{(3-butylcyclohexyl)hexyl}cyclohexylaldehyde pentaerythritol acetal, 2-{(3-butylcyclohexyl)hexyl}cyclohexylaldehyde pentaerythritol acetal, 4-{(3-butylcyclohexyl)heptyl}cyclohexylaldehyde pentaerythritol acetal, 3-{(3-butylcyclohexyl)heptyl}cyclohexylaldehyde pentaerythritol acetal, 2-{(3-butylcyclohexyl)heptyl}cyclohexylaldehyde pentaerythritol acetal, 4-{(3-butylcyclohexyl)octyl}cyclohexylaldehyde pentaerythritol acetal, 3-{(3-butylcyclohexyl)octyl}cyclohexylaldehyde pentaerythritol acetal, 2-{(3-butylcyclohexyl)octyl}cyclohexylaldehyde pentaerythritol acetal, 4-{(3-butylcyclohexyl)nonyl}cyclohexylaldehyde pentaerythritol acetal, 3-{(3-butylcyclohexyl)nonyl}cyclohexylaldehyde pentaerythritol acetal, 2-{(3-butylcyclohexyl)nonyl}cyclohexylaldehyde pentaerythritol acetal, 4-{(3-butylcyclohexyl)decanyl}cyclohexylaldehyde pentaerythritol acetal, 3-{(3-butylcyclohexyl)decanyl}cyclohexylaldehyde pentaerythritol acetal, 2-{(3-butylcyclohexyl)decanyl}cyclohexylaldehyde pentaerythritol acetal, 4-(2,4-dimethylcyclohexyl)cyclohexylaldehyde pentaerythritol acetal, 3-(2,4-dimethylcyclohexyl)cyclohexylaldehyde pentaerythritol acetal, 2-(2,4-dimethylcyclohexyl)cyclohexylaldehyde pentaerythritol acetal, 4-{(2,4-dimethylcyclohexyl)methyl}cyclohexylaldehyde pentaerythritol acetal, 3-{(2,4-dimethylcyclohexyl)methyl}cyclohexylaldehyde pentaerythritol acetal, 2-{(2,4-dimethylcyclohexyl)methyl}cyclohexylaldehyde pentaerythritol acetal, 4-{(2,4-dimethylcyclohexyl)ethyl}cyclohexylaldehyde pentaerythritol acetal, 3-{(2,4-dimethylcyclohexyl)ethyl}cyclohexylaldehyde pentaerythritol acetal, 2-{(2,4-dimethylcyclohexyl)ethyl}cyclohexylaldehyde pentaerythritol acetal, 4-{(2,4-dimethylcyclohexyl)propyl}cyclohexylaldehyde pentaerythritol acetal, 3-{(2,4-dimethylcyclohexyl)propyl}cyclohexylaldehyde pentaerythritol acetal, 2-{(2,4-dimethylcyclohexyl)propyl}cyclohexylaldehyde pentaerythritol acetal, 4-{(2,4-dimethylcyclohexyl)butyl}cyclohexylaldehyde pentaerythritol acetal, 3-{(2,4-dimethylcyclohexyl)butyl}cyclohexylaldehyde pentaerythritol acetal, 2-{(2,4-dimethylcyclohexyl)butyl}cyclohexylaldehyde pentaerythritol acetal, 4-{(2,4-dimethylcyclohexyl)pentyl}cyclohexylaldehyde pentaerythritol acetal, 3-{(2,4-dimethylcyclohexyl)pentyl}cyclohexylaldehyde pentaerythritol acetal, 2-{(2,4-dimethylcyclohexyl)pentyl}cyclohexylaldehyde pentaerythritol acetal, 4-{(2,4-dimethylcyclohexyl)hexyl}cyclohexylaldehyde pentaerythritol acetal, 3-{(2,4-dimethylcyclohexyl)hexyl}cyclohexylaldehyde pentaerythritol acetal, 2-{(2,4-dimethylcyclohexyl)hexyl}cyclohexylaldehyde pentaerythritol acetal, 4-{(2,4-dimethylcyclohexyl)heptyl}cyclohexylaldehyde pentaerythritol acetal, 3-{(2,4-dimethylcyclohexyl)heptyl}cyclohexylaldehyde pentaerythritol acetal, 2-{(2,4-dimethylcyclohexyl)heptyl}cyclohexylaldehyde pentaerythritol acetal, 4-{(2,4-dimethylcyclohexyl)octyl}cyclohexylaldehyde pentaerythritol acetal, 3-{(2,4-dimethylcyclohexyl)octyl}cyclohexylaldehyde pentaerythritol acetal, 2-{(2,4-dimethylcyclohexyl)octyl}cyclohexylaldehyde pentaerythritol acetal, 4-{(2,4-dimethylcyclohexyl)nonyl}cyclohexylaldehyde pentaerythritol acetal, 3-{(2,4-dimethylcyclohexyl)nonyl}cyclohexylaldehyde pentaerythritol acetal, 2-{(2,4-dimethylcyclohexyl)nonyl}cyclohexylaldehyde pentaerythritol acetal, 4-{(2,4-dimethylcyclohexyl)decanyl}cyclohexylaldehyde pentaerythritol acetal, 3-{(2,4-dimethylcyclohexyl)decanyl}cyclohexylaldehyde pentaerythritol acetal, 2-{(2,4-dimethylcyclohexyl)decanyl}cyclohexylaldehyde pentaerythritol acetal, 4-(3,4-dimethylcyclohexyl)cyclohexylaldehyde pentaerythritol acetal, 3-(3,4-dimethylcyclohexyl)cyclohexylaldehyde pentaerythritol acetal, 2-(3,4-dimethylcyclohexyl)cyclohexylaldehyde pentaerythritol acetal, 4-{(3,4-dimethylcyclohexyl)methyl}cyclohexylaldehyde pentaerythritol acetal, 3-{(3,4-dimethylcyclohexyl)methyl}cyclohexylaldehyde pentaerythritol acetal, 2-{(3,4-dimethylcyclohexyl)methyl}cyclohexylaldehyde pentaerythritol acetal, 4-{(3,4-dimethylcyclohexyl)ethyl}cyclohexylaldehyde pentaerythritol acetal, 3-{(3,4-dimethylcyclohexyl)ethyl}cyclohexylaldehyde pentaerythritol acetal, 2-{(3,4-dimethylcyclohexyl)ethyl}cyclohexylaldehyde pentaerythritol acetal, 4-{(3,4-dimethylcyclohexyl)propyl}cyclohexylaldehyde pentaerythritol acetal, 3-{(3,4-dimethylcyclohexyl)propyl}cyclohexylaldehyde pentaerythritol acetal, 2-{(3,4-dimethylcyclohexyl)propyl}cyclohexylaldehyde pentaerythritol acetal, 4-{(3,4-dimethylcyclohexyl)butyl}cyclohexylaldehyde pentaerythritol acetal, 3-{(3,4-dimethylcyclohexyl)butyl}cyclohexylaldehyde pentaerythritol acetal, 2-{(3,4-dimethylcyclohexyl)butyl}cyclohexylaldehyde pentaerythritol acetal, 4-{(3,4-dimethylcyclohexyl)pentyl}cyclohexylaldehyde pentaerythritol acetal, 3-{(3,4-dimethylcyclohexyl)pentyl}cyclohexylaldehyde pentaerythritol acetal, 2-{(3,4-dimethylcyclohexyl)pentyl}cyclohexylaldehyde pentaerythritol acetal, 4-{(3,4-dimethylcyclohexyl)hexyl}cyclohexylaldehyde pentaerythritol acetal, 3-{(3,4-dimethylcyclohexyl)hexyl}cyclohexylaldehyde pentaerythritol acetal, 2-{(3,4-dimethylcyclohexyl)hexyl}cyclohexylaldehyde pentaerythritol acetal, 4-{(3,4-dimethylcyclohexyl)heptyl}cyclohexylaldehyde pentaerythritol acetal, 3-{(3,4-dimethylcyclohexyl)heptyl}cyclohexylaldehyde pentaerythritol acetal, 2-{(3,4-dimethylcyclohexyl)heptyl}cyclohexylaldehyde pentaerythritol acetal, 4-{(3,4-dimethylcyclohexyl)octyl}cyclohexylaldehyde pentaerythritol acetal, 3-{(3,4-dimethylcyclohexyl)octyl}cyclohexylaldehyde pentaerythritol acetal, 2-{(3,4-dimethylcyclohexyl)octyl}cyclohexylaldehyde pentaerythritol acetal, 4-{(3,4-dimethylcyclohexyl)nonyl}cyclohexylaldehyde pentaerythritol acetal, 3-{(3,4-dimethylcyclohexyl)nonyl}cyclohexylaldehyde pentaerythritol acetal, 2-{(3,4-dimethylcyclohexyl)nonyl}cyclohexylaldehyde pentaerythritol acetal, 4-{(3,4-dimethylcyclohexyl)decanyl}cyclohexylaldehyde pentaerythritol acetal, 3-{(3,4-dimethylcyclohexyl)decanyl}cyclohexylaldehyde pentaerythritol acetal, 2-{(3,4-dimethylcyclohexyl)decanyl}cyclohexylaldehyde pentaerythritol acetal, 4-(2,3-dimethylcyclohexyl)cyclohexylaldehyde pentaerythritol acetal, 3-(2,3-dimethylcyclohexyl)cyclohexylaldehyde pentaerythritol acetal, 2-(2,3-dimethylcyclohexyl)cyclohexylaldehyde pentaerythritol acetal, 4-{(2,3-dimethylcyclohexyl)methyl}cyclohexylaldehyde pentaerythritol acetal, 3-{(2,3-dimethylcyclohexyl)methyl}cyclohexylaldehyde pentaerythritol acetal, 2-{(2,3-dimethylcyclohexyl)methyl}cyclohexylaldehyde pentaerythritol acetal, 4-{(2,3-dimethylcyclohexyl)ethyl}cyclohexylaldehyde pentaerythritol acetal, 3-{(2,3-dimethylcyclohexyl)ethyl}cyclohexylaldehyde pentaerythritol acetal, 2-{(2,3-dimethylcyclohexyl)ethyl}cyclohexylaldehyde pentaerythritol acetal, 4-{(2,3-dimethylcyclohexyl)propyl}cyclohexylaldehyde pentaerythritol acetal, 3-{(2,3-dimethylcyclohexyl)propyl}cyclohexylaldehyde pentaerythritol acetal, 2-{(2,3-dimethylcyclohexyl)propyl}cyclohexylaldehyde pentaerythritol acetal, 4-{(2,3-dimethylcyclohexyl)butyl}cyclohexylaldehyde pentaerythritol acetal, 3-{(2,3-dimethylcyclohexyl)butyl}cyclohexylaldehyde pentaerythritol acetal, 2-{(2,3-dimethylcyclohexyl)butyl}cyclohexylaldehyde pentaerythritol acetal, 4-{(2,3-dimethylcyclohexyl)pentyl}cyclohexylaldehyde pentaerythritol acetal, 3-{(2,3-dimethylcyclohexyl)pentyl}cyclohexylaldehyde pentaerythritol acetal, 2-{(2,3-dimethylcyclohexyl)pentyl}cyclohexylaldehyde pentaerythritol acetal, 4-{(2,3-dimethylcyclohexyl)hexyl}cyclohexylaldehyde pentaerythritol acetal, 3-{(2,3-dimethylcyclohexyl)hexyl}cyclohexylaldehyde pentaerythritol acetal, 2-{(2,3-dimethylcyclohexyl)hexyl}cyclohexylaldehyde pentaerythritol acetal, 4-{(2,3-dimethylcyclohexyl)heptyl}cyclohexylaldehyde pentaerythritol acetal, 3-{(2,3-dimethylcyclohexyl)heptyl}cyclohexylaldehyde pentaerythritol acetal, 2-{(2,3-dimethylcyclohexyl)

heptyl}cyclohexylaldehyde pentaerythritol acetal, 4-{(2,3-dimethylcyclohexyl)octyl}cyclohexylaldehyde pentaerythritol acetal, 3-{(2,3-dimethylcyclohexyl)octyl}cyclohexylaldehyde pentaerythritol acetal, 2-{(2,3-dimethylcyclohexyl)octyl}cyclohexylaldehyde pentaerythritol acetal, 4-{(2,3-dimethylcyclohexyl)nonyl}cyclohexylaldehyde pentaerythritol acetal, 3-{(2,3-dimethylcyclohexyl)nonyl}cyclohexylaldehyde pentaerythritol acetal, 2-{(2,3-dimethylcyclohexyl)nonyl}cyclohexylaldehyde pentaerythritol acetal, 4-{(2,3-dimethylcyclohexyl)decanyl}cyclohexylaldehyde pentaerythritol acetal, 3-{(2,3-dimethylcyclohexyl)decanyl}cyclohexylaldehyde pentaerythritol acetal, 2-{(2,3-dimethylcyclohexyl)decanyl}cyclohexylaldehyde pentaerythritol acetal, 4-(3,5-dimethylcyclohexyl)cyclohexylaldehyde pentaerythritol acetal, 3-(3,5-dimethylcyclohexyl)cyclohexylaldehyde pentaerythritol acetal, 2-(3,5-dimethylcyclohexyl)cyclohexylaldehyde pentaerythritol acetal, 4-{(3,5-dimethylcyclohexyl)methyl}cyclohexylaldehyde pentaerythritol acetal, 3-{(3,5-dimethylcyclohexyl)methyl}cyclohexylaldehyde pentaerythritol acetal, 2-{(3,5-dimethylcyclohexyl)methyl}cyclohexylaldehyde pentaerythritol acetal, 4-{(3,5-dimethylcyclohexyl)ethyl}cyclohexylaldehyde pentaerythritol acetal, 3-{(3,5-dimethylcyclohexyl)ethyl}cyclohexylaldehyde pentaerythritol acetal, 2-{(3,5-dimethylcyclohexyl)ethyl}cyclohexylaldehyde pentaerythritol acetal, 4-{(3,5-dimethylcyclohexyl)propyl}cyclohexylaldehyde pentaerythritol acetal, 3-{(3,5-dimethylcyclohexyl)propyl}cyclohexylaldehyde pentaerythritol acetal, 2-{(3,5-dimethylcyclohexyl)propyl}cyclohexylaldehyde pentaerythritol acetal, 4-{(3,5-dimethylcyclohexyl)butyl}cyclohexylaldehyde pentaerythritol acetal, 3-{(3,5-dimethylcyclohexyl)butyl}cyclohexylaldehyde pentaerythritol acetal, 2-{(3,5-dimethylcyclohexyl)butyl}cyclohexylaldehyde pentaerythritol acetal, 4-{(3,5-dimethylcyclohexyl)pentyl}cyclohexylaldehyde pentaerythritol acetal, 3-{(3,5-dimethylcyclohexyl)pentyl}cyclohexylaldehyde pentaerythritol acetal, 2-{(3,5-dimethylcyclohexyl)pentyl}cyclohexylaldehyde pentaerythritol acetal, 4-{(3,5-dimethylcyclohexyl)hexyl}cyclohexylaldehyde pentaerythritol acetal, 3-{(3,5-dimethylcyclohexyl)hexyl}cyclohexylaldehyde pentaerythritol acetal, 2-{(3,5-dimethylcyclohexyl)hexyl}cyclohexylaldehyde pentaerythritol acetal, 4-{(3,5-dimethylcyclohexyl)heptyl}cyclohexylaldehyde pentaerythritol acetal, 3-{(3,5-dimethylcyclohexyl)heptyl}cyclohexylaldehyde pentaerythritol acetal, 2-{(3,5-dimethylcyclohexyl)heptyl}cyclohexylaldehyde pentaerythritol acetal, 4-{(3,5-dimethylcyclohexyl)octyl}cyclohexylaldehyde pentaerythritol acetal, 3-{(3,5-dimethylcyclohexyl)octyl}cyclohexylaldehyde pentaerythritol acetal, 2-{(3,5-dimethylcyclohexyl)octyl}cyclohexylaldehyde pentaerythritol acetal, 4-{(3,5-dimethylcyclohexyl)nonyl}cyclohexylaldehyde pentaerythritol acetal, 3-{(3,5-dimethylcyclohexyl)nonyl}cyclohexylaldehyde pentaerythritol acetal, 2-{(3,5-dimethylcyclohexyl)nonyl}cyclohexylaldehyde pentaerythritol acetal, 4-{(3,5-dimethylcyclohexyl)decanyl}cyclohexylaldehyde pentaerythritol acetal, 3-{(3,5-dimethylcyclohexyl)decanyl}cyclohexylaldehyde pentaerythritol acetal, 2-{(3,5-dimethylcyclohexyl)decanyl}cyclohexylaldehyde pentaerythritol acetal, 4-(2,6-dimethylcyclohexyl)cyclohexylaldehyde pentaerythritol acetal, 3-(2,6-dimethylcyclohexyl)cyclohexylaldehyde pentaerythritol acetal, 2-(2,6-dimethylcyclohexyl)cyclohexylaldehyde pentaerythritol acetal, 4-{(2,6-dimethylcyclohexyl)methyl}cyclohexylaldehyde pentaerythritol acetal, 3-{(2,6-dimethylcyclohexyl)methyl}cyclohexylaldehyde pentaerythritol acetal, 2-{(2,6-dimethylcyclohexyl)methyl}cyclohexylaldehyde pentaerythritol acetal, 4-{(2,6-dimethylcyclohexyl)ethyl}cyclohexylaldehyde pentaerythritol acetal, 3-{(2,6-dimethylcyclohexyl)ethyl}cyclohexylaldehyde pentaerythritol acetal, 2-{(2,6-dimethylcyclohexyl)ethyl}cyclohexylaldehyde pentaerythritol acetal, 4-{(2,6-dimethylcyclohexyl)propyl}cyclohexylaldehyde pentaerythritol acetal, 3-{(2,6-dimethylcyclohexyl)propyl}cyclohexylaldehyde pentaerythritol acetal, 2-{(2,6-dimethylcyclohexyl)propyl}cyclohexylaldehyde pentaerythritol acetal, 4-{(2,6-dimethylcyclohexyl)butyl}cyclohexylaldehyde pentaerythritol acetal, 3-{(2,6-dimethylcyclohexyl)butyl}cyclohexylaldehyde pentaerythritol acetal, 2-{(2,6-dimethylcyclohexyl)butyl}cyclohexylaldehyde pentaerythritol acetal, 4-{(2,6-dimethylcyclohexyl)pentyl}cyclohexylaldehyde pentaerythritol acetal, 3-{(2,6-dimethylcyclohexyl)pentyl}cyclohexylaldehyde pentaerythritol acetal, 2-{(2,6-dimethylcyclohexyl)pentyl}cyclohexylaldehyde pentaerythritol acetal, 4-{(2,6-dimethylcyclohexyl)hexyl}cyclohexylaldehyde pentaerythritol acetal, 3-{(2,6-dimethylcyclohexyl)hexyl}cyclohexylaldehyde pentaerythritol acetal, 2-{(2,6-dimethylcyclohexyl)hexyl}cyclohexylaldehyde pentaerythritol acetal, 4-{(2,6-dimethylcyclohexyl)heptyl}cyclohexylaldehyde pentaerythritol acetal, 3-{(2,6-dimethylcyclohexyl)heptyl}cyclohexylaldehyde pentaerythritol acetal, 2-{(2,6-dimethylcyclohexyl)heptyl}cyclohexylaldehyde pentaerythritol acetal, 4-{(2,6-dimethylcyclohexyl)octyl}cyclohexylaldehyde pentaerythritol acetal, 3-{(2,6-dimethylcyclohexyl)octyl}cyclohexylaldehyde pentaerythritol acetal, 2-{(2,6-dimethylcyclohexyl)octyl}cyclohexylaldehyde pentaerythritol acetal, 4-{(2,6-dimethylcyclohexyl)nonyl}cyclohexylaldehyde pentaerythritol acetal, 3-{(2,6-dimethylcyclohexyl)nonyl}cyclohexylaldehyde pentaerythritol acetal, 2-{(2,6-dimethylcyclohexyl)nonyl}cyclohexylaldehyde pentaerythritol acetal, 4-{(2,6-dimethylcyclohexyl)decanyl}cyclohexylaldehyde pentaerythritol acetal, 3-{(2,6-dimethylcyclohexyl)decanyl}cyclohexylaldehyde pentaerythritol acetal, 2-{(2,6-dimethylcyclohexyl)decanyl}cyclohexylaldehyde pentaerythritol acetal and so on. 2-bicyclohexylaldehyde pentaerythritol acetal, 3-bicyclohexylaldehyde pentaerythritol acetal and 4-bicyclohexylaldehyde pentaerythritol acetal are preferable, and 4-bicyclohexylaldehyde pentaerythritol acetal is more preferable. The acetal compound (A4) of the carbonyl compound may have a linear or branched alkyl group having a carbon number of 1 to 4, cyano group, hydroxyl group, a halogen atom and so on within a range not damaging the effect of the invention. The ethylene acetal compounds (A4) of the carbonyl compound may be used alone or in a combination of two or more.

The carbonyl compound (A1) is obtained by hydrogenating a corresponding compound having a benzene ring to convert into cyclohexyl ring.

There are well-known methods as the hydrogenation, and the carbonyl compound is obtained by the reaction in the presence of hydrogen using ruthenium/alumina catalyst, palladium/alumina catalyst, lanthanum series catalyst, palladium/carbon catalyst, rhodium/titanium dioxide catalyst, ruthenium dioxide catalyst, rhodium/alumina catalyst, platinum series catalyst, ruthenium/carbon catalyst or the like.

The carbonyl compound (A1) can be protected with an acetal group and is stabilized by acetal protection. The acetal protection can be conducted by the well-known method. For example, the carbonyl compound (A1) can be protected with an acetal group by reacting with a bivalent alcohol in the presence of an acid.

As an example of the phenolic compound (A2) are mentioned phenol, catechol, resorcinol, hydroquinone, pyrogallol and the like. Resorcinol and pyrogallol are preferable, and resorcinol is more preferable. The phenolic compound (A2) may have a linear or branched alkyl group having a carbon number of 1 to 4, cyano group, hydroxyl group, a halogen atom and the like within a range not damaging the effect of the invention. The phenolic compounds (A2) may be used alone or in a combination of two or more.

The cyclic compound represented by the formula (1) can be produced by a well-known method. For example, the cyclic compound (A) is obtained by reacting 1 mol of the carbonyl compound (A1) or the acetal compound of the carbonyl compound (A4) with 0.1 to 10 mol of the phenolic compound (A2) in an organic solvent such as methanol, ethanol or the like with an acid catalyst (hydrochloric acid, sulfuric acid, p-toluenesulfonic acid or the like) at 60 to 150° C. for about 0.5 to 20 hours, washing the resulting product after filtration with an alcohol such as methanol or the like, washing with water, separating through filtration and drying it. Alternatively, the cyclic compound (A) may be obtained by the same reaction using a basic catalyst (sodium hydroxide, barium hydroxide, 1,8-diazabicyclo[5.4.0]undecene-7 or the like) instead of the acid catalyst.

It is more preferable to use two or more kinds of the carbonyl compounds (A1) and/or two or more kinds of the acetal compounds of the carbonyl compound (A4) and/or two or more kinds of the phenolic compounds (A2). By using two or more kinds of the carbonyl compounds (A1) and/or two or more kinds of the acetal compounds of the carbonyl compound (A4) and/or two or more kinds of the phenolic compounds (A2) is improved the solubility of the resulting cyclic compound in semiconductor safety solvents.

The cyclic compound according to the invention may be purified to reduce the amount of residual metal, if necessary. If the acid catalyst and co-catalyst remain, the storage stability of the radiation sensitive composition is generally lowered, or if the basic catalyst remains, the sensitivity of the radiation sensitive composition is generally lowered, so that the purification may be conducted for the purpose of reducing the remaining amount of the catalyst. The purification may be carried out by any of known methods without limitation as long as the cyclic compound is not modified, which includes, for example, a method of washing with water, a method of washing with an acidic aqueous solution, a method of washing with a basic aqueous solution, a method of treating with an ion exchange resin, a method of treating with a silica gel column chromatography and so on. The purification is preferably conducted in a combination of two or more of the above methods. The acidic aqueous solution, basic aqueous solution, ion exchange resin and silica gel column may be properly selected depending upon the amount and kind of the metal, acidic compound and basic compound to be removed and the kind of the cyclic compound to be purified. For example, as the acidic aqueous solution is mentioned an aqueous solution of hydrochloric acid, nitric acid or acetic acid having a concentration of 0.01 to 10 mol/L, and as the basic aqueous solution is mentioned an aqueous solution of ammonia having a concentration of 0.01 to 10 mol/L, and as the ion exchange resin is mentioned a cation exchange resin such as Amberlyst 15J-HG Dry manufactured by Organo Corporation. The drying may be conducted after the purification. The drying can be carried out by a well-known method such as, but not limited to, a vacuum drying and a hot-air drying under the conditions not changing the cyclic compound.

The cyclic compound represented by the formula (1) can form an amorphous film with spin coating. Also, it is applicable to a general semiconductor production process.

The cyclic compound represented by the formula (1) is useful as a negative-type resist material which is made into a compound hardly-soluble in an alkali developing solution by the irradiation of KrF excimer laser, extreme ultraviolet ray, electron beams or X-ray. It is considered due to the fact that condensation reaction of the cyclic compound is induced by the irradiation of KrF excimer laser, extreme ultraviolet ray, electron beams or X-ray to convert into a compound hardly-soluble in an alkali developing solution. The thus obtained resist pattern is very small in LER.

The cyclic compound according to the invention represented by the formula (1) may be used as a main component of a negative-type radiation sensitive composition or may be added to a radiation sensitive composition as an additive for increasing the sensitivity and improving the etching resistance instead of using as the main component. In this case, the cyclic compound is used in an amount of 1 to 49.999% by weight of the total weight of the solid component.

The dissolving speed of the amorphous film of the cyclic compound according to the invention at 23° C. in an aqueous solution of 2.38 mass % of tetramethylammonium hydroxide (TMAH) is preferably not less than 10 Å/sec, more preferably 10 to 10000 Å/sec, and still more preferably 100 to 1000 Å/sec. When the dissolving speed is not less than 10 Å/sec, the amorphous film can be dissolved in an alkali developing solution to form a resist. If the dissolving speed is not more than 10000 Å/sec, the resolution may be improved. This is guessed due to the fact that the contrast at the interface between the non-exposed portion soluble in an alkali developing solution and the exposed portion insoluble in an alkali developing solution is enhanced by the change of solubility before and after exposing the cyclic compound to radiation. In addition, there are an effect of reducing LER and an effect of reducing the number of defects.

The glass transition temperature of the cyclic compound according to the invention is preferably not lower than 100° C., more preferably not lower than 120° C., still more preferably not lower than 140° C., and particularly preferably not lower than 150° C. When the glass transition temperature is within the above range, the cyclic compound has a heat resistance capable of maintaining the pattern shape in the semiconductor lithographic process and can give performances such as high resolution and the like.

The amount of crystallization heat of the cyclic compound (d) is preferably less than 20 J/g as determined by a differential scanning calorimetry of the glass transition temperature. Also, the value of (crystallization temperature)−(glass transition temperature) is preferably not lower than 70° C., more preferably not lower than 80° C., still more preferably not lower than 100° C., and particularly preferably not lower than 130° C. When the amount of crystallization heat is less than 20 J/g or the value of (crystallization temperature)−(glass transition temperature) is within the above range, the radiation sensitive composition easily forms an amorphous film with spin coating and cam maintain the film-forming properties required for the resist over a long period of time to improve the resolution.

In the invention, the amount of crystallization heat, crystallization temperature and glass transition temperature can be determined by measurement and differential scanning calorimetry using DSC/TA-50WS manufactured by Shimadzu Corporation as described below. About 10 mg of a sample is placed in a non-sealed aluminum container and heated to a temperature above a melting point at a temperature rising rate of 20° C./min in a nitrogen gas flow (50 ml/min). After rapid cooling, the sample is again heated to a temperature above the melting point at a temperature rising rate of 20° C./min in a nitrogen gas flow (30 ml/min). After further rapid cooling, the sample is again heated to 400° C. at a temperature rising rate of 20° C./min in a nitrogen gas flow (30 ml/min). A temperature at a middle point of a zone developing discontinuous portion on a base line (the point at which the specific heat reduces to half) is taken as a glass transition temperature (Tg), and a temperature of a subsequently developed exothermic peak is taken as a crystallization temperature. The amount of crystallization heat is determined by measuring heat quantity from the area of the region surrounded by the exothermic peak and the base line.

The cyclic compound according to the invention is preferable to have a low sublimation under atmospheric pressure at 100° C. or lower, preferably at 120° C. or lower, more preferably at 130° C. or lower, still more preferably at 140° C. or lower, and particularly preferably at 150° C. or lower. The low sublimation means that the weight reduction through a thermogravimetric analysis when being kept at a predetermined temperature for 10 min is 10%, preferably 5%, more preferably 3%, still more preferably 1%, and particularly preferably not more than 0.1%. The contamination of the exposure apparatus by the outgas generated in the exposing process can be prevented by the low sublimation. In addition, the good pattern shape can be given by low LER.

The cyclic compound according to the invention satisfies preferably the requirement of F<3.0 (F is indicates (total number of atoms)/(total number of carbon atoms−total number of oxygen atoms)), and more preferably F<2.5. By satisfying the above conditions, the resistance to dry-etching becomes excellent.

The cyclic compound according to the invention is dissolved at 23° C. in a solvent selected from propylene glycol monomethyl ether acetate (PGMEA), propylene glycol monomethyl ether (PGME), cyclohexanone (CHN), cyclopentanone (CPN), 2-heptanone, anisole, butyl acetate, ethyl propionate and ethyl lactate at an amount of preferably not less than 1% by weight, more preferably not less than 5% by weight, still more preferably not less than 10% by weight, and particularly preferably at 23° C. in a solvent selected from PGMEA, PGME and CHN and having the highest dissolving capacity to the cyclic compound at an amount of not less than 20% by weight, and particularly preferably at 23° C. in PGMEA at an amount of not less than 20% by weight. With satisfying such conditions, the cyclic compound can be used at the semiconductor manufacturing step in the actual production.

A halogen atom may be introduced into the cyclic compound according to the invention within a range not damaging the effect of the invention. The ratio of the number of halogen atoms to the total number of constituent atoms of the cyclic compound is preferably 0.1 to 60%, more preferably 0.1 to 40%, still more preferably 0.1 to 20%, particularly preferably 0.1 to 10%, and most preferably 1 to 5%. When the ratio of halogen atom is within the above range, the film-forming properties can be maintained while increasing the sensitivity to radiation. In addition, the solubility in safety solvents can be increased.

A nitrogen atom may be introduced into the cyclic compound according to the invention within a range not damaging the effect of the invention. The ratio of the number of nitrogen atoms to the total number of constituent atoms of the cyclic compound is preferably 0.1 to 40%, more preferably 0.1 to 20%, still more preferably 0.1 to 10%, and particularly preferably 0.1 to 5%. When the ratio of nitrogen atom is within the above range, the line edge roughness of the resulting resist pattern can be reduced. As the nitrogen atom is preferable nitrogen atom included in a secondary or tertiary amine, and more preferable nitrogen atom included in a tertiary amine.

A crosslinking reactive group causing a crosslinking reaction by the irradiation with visible light, ultraviolet ray, excimer laser, electron beams, extreme ultraviolet ray (EUV), X-ray or ion beams or by the chemical reaction induced thereby may be introduced into the cyclic compound according to the invention within a range not damaging the effect of the invention. For example, the introduction is conducted by reacting the cyclic compound with an introducing agent for the crosslinking reactive group in the presence of a base catalyst. As the crosslinking reactive group are mentioned a carbon-carbon multiple bond, an epoxy group, an azide group, a halogenated phenyl group and chloromethyl group. As the introducing agent for the crosslinking reactive group are mentioned an acid having such a crosslinking reactive group, an acid chloride, an acid anhydride, a derivative of carboxylic acid such as dicarbonate or the like, an alkyl halide and so on. A radiation sensitive composition containing the cyclic compound having a crosslinking reactive group is also useful as a non-polymer radiation sensitive composition with a high resolution, high heat resistance and solvent-solubility.

A non-acid-dissociating functional group may be introduced into at least one phenolic hydroxyl group of the cyclic compound according to the invention within a range not damaging the effect of the invention. The non-acid-dissociating functional group means a characteristic group which is not cleavaged in the presence of an acid and does not generate an alkali-soluble group. As such a group are mentioned, for example, groups selected from the group consisting of C1-20 alkyl groups, C3-20 cycloalkyl groups, C6-20 aryl groups, C1-20 alkoxyl groups, cyano group, nitro group, hydroxyl group, heterocyclic group, halogen, carboxyl groups, C1-20 alkylsilanes and derivatives thereof, which are not decomposed by the action of acid.

A naphthoquinonediazido ester group may be introduced into at least one phenolic hydroxyl group of the cyclic compound according to the invention within a range not damaging the effect of the invention. The compound wherein the naphthoquinonediazido ester group is introduced into at least one phenolic hydroxyl group of the cyclic compound may be used as the main component of a negative-type radiation sensitive composition or as the main component of a positive-type radiation sensitive composition, or may be added to a radiation sensitive composition as an acid generator or an additive.

An acid-generating functional group generating an acid upon the irradiation with radiation may be introduced into at least one phenolic hydroxyl group of the cyclic compound according to the invention within a range not damaging the effect of the invention. The cyclic polyphenol compound wherein the acid-generating functional group generating an acid upon the irradiation with radiation is introduced into at least one phenolic hydroxyl group of the cyclic compound may be used as the main component of a negative-type radiation sensitive composition or as the main component of a positive-type radiation sensitive composition, or may be added to a radiation sensitive composition as an acid generator or an additive.

[Radiation Sensitive Composition]

The invention relates to a radiation sensitive composition comprising the cyclic compound represented by the formula (1) and a solvent.

Also, the invention is preferable to be a radiation sensitive composition consisting of 1 to 80% by weight of a solid component and 20 to 99% by weight of a solvent, and is more preferably a radiation sensitive composition wherein the cyclic compound is 50 to 99.999% by weight based on the total weight of the solid component.

The cyclic compound according to the invention can form an amorphous film with spin coating, and can be applied to a general semiconductor production process.

The dissolving speed of the amorphous film of the cyclic compound according to the invention at 23° C. in an aqueous solution of 2.38 mass % of tetramethylammonium hydroxide (TMAH) is preferably not less than 10 Å/sec, more preferably 10 to 10000 Å/sec, and still more preferably 100 to 1000 Å/sec. When the dissolving speed is not less than 10 Å/sec, the amorphous film can be dissolved in an alkali developing solution to form a resist. Also, when the dissolving speed is not more than 10000 Å/sec or less, the resolution may be improved. This is guessed due to the fact that the contrast at the interface between the non-exposed portion soluble in an alkali developing solution and the exposed portion insoluble in an alkali developing solution is enhanced by the change of solubility before and after exposing the cyclic compound to radiation. In addition, there are effects of reducing LER and of reducing the number of defects.

A crosslinking reactive group causing a crosslinking reaction by the irradiation with visible light, ultraviolet ray, excimer laser, electron beams, extreme ultraviolet ray (EUV), X-ray or ion beams, or by the chemical reaction induced thereby may be introduced into the cyclic compound according to the invention within a range not damaging the effect of the invention. For example, the introduction is conducted by reacting the cyclic compound with an introducing agent for the crosslinking reactive group in the presence of a base catalyst. As the crosslinking reactive group are mentioned a carbon-carbon multiple bond, an epoxy group, an azido group, a halogenated phenyl group and chloromethyl group. As the introducing agent for the crosslinking reactive group are mentioned an acid having such a crosslinking reactive group, an acid chloride, an acid anhydride, a derivative of carboxylic acid such as dicarbonate, an alkyl halide and so on. A radiation sensitive composition containing the cyclic compound having a crosslinking reactive group is also useful as a non-polymer radiation sensitive composition with a high resolution, high heat resistance and solvent-solubility.

A non-acid-dissociating functional group may be introduced into at least one phenolic hydroxyl group of the cyclic compound according to the invention within a range not damaging the effect of the invention. The non-acid-dissociating functional group means a characteristic group which is not cleavaged in the presence of acid and does not generate an alkali-soluble group. As the group are mentioned, for example, groups selected from the group consisting of C1-20 alkyl groups, C3-20 cycloalkyl groups, C6-20 aryl groups, C1-20 alkoxyl groups, cyano group, nitro group, hydroxyl group, heterocyclic group, halogen, carboxyl group, C1-20 alkylsilanes, derivatives thereof and so on which are not decomposed by the action of acid.

A naphthoquinonediazido ester group may be introduced into at least one phenolic hydroxyl group of the cyclic compound according to the invention within a range not damaging the effect of the invention. The compound wherein the naphthoquinonediazido ester group is introduced into at least one phenolic hydroxyl group of the cyclic compound may be used as the main component of a negative-type radiation sensitive composition or as the main component of a positive-type radiation sensitive composition, or may be added to a radiation sensitive composition as an acid generator or an additive.

An acid-generating functional group generating an acid upon the irradiation with radiation may be introduced into at least one phenolic hydroxyl group of the cyclic compound according to the invention within a range not damaging the effect of the invention. The cyclic polyphenol compound wherein the acid-generating functional group generating an acid upon the irradiation with radiation is introduced into at least one phenolic hydroxyl group of the cyclic compound may be used as the main component of a negative-type radiation sensitive composition or as the main component of a positive-type radiation sensitive composition, or may be added to a radiation sensitive composition as an acid generator or an additive.

A halogen atom may be introduced into the cyclic compound according to the invention within a range not damaging the effect of the invention. The ratio of the number of halogen atoms to the total number of constituent atoms of the cyclic compound is preferably 0.1 to 60%, more preferably 0.1 to 40%, still more preferably 0.1 to 20%, particularly preferably 0.1 to 10%, and most preferably 1 to 5%. When the ratio of the halogen atom is within the above range, the film-forming properties can be maintained while increasing the sensitivity to radiation. In addition, the solubility in safety solvents can be increased.

A nitrogen atom may be introduced into the cyclic compound according to the invention within a range not damaging the effect of the invention. The ratio of the number of nitrogen atoms to the total number of constituent atoms of the cyclic compound is preferably 0.1 to 40%, more preferably 0.1 to 20%, still more preferably 0.1 to 10%, and particularly preferably 0.1 to 5%. When the ratio of nitrogen atom is within the above range, the line edge roughness of the resulting resist pattern can be reduced. As the nitrogen atom is preferable nitrogen atom included in a secondary or tertiary amine, and more preferable nitrogen atom included in a tertiary amine.

The radiation sensitive composition according to the invention can form an amorphous film with spin coating. The dissolving speed of the amorphous film formed by spin coating the radiation sensitive composition according to the invention in an aqueous solution of 2.38% by mass of TMAH at 23° C. is preferably not less than 10 Å/sec, more preferably 10 to 10000 Å/sec, and still more preferably 100 to 1000 Å/sec. When the dissolving speed is not less than 10 Å/sec, the amorphous film can be dissolved in an alkali developing solution to form a resist. If the dissolving speed is not more than 10000 Å/sec, the resolution may be improved. This is guessed due to the fact that the contrast at the interface between the non-exposed portion soluble in an alkali developing solution and the exposed portion insoluble in an alkali developing solution is enhanced by the change of solubility before and after exposing the cyclic compound to radiation. In addition, there are effects of reducing LER and reducing the number of defects.

The dissolving speed of the area exposed to a radiation such as KrF excimer laser, extreme ultraviolet ray, electron beams and X-ray in the amorphous film, which is formed by spin coating of the solid component in the radiation sensitive component according to the invention, in an aqueous solution of 2.38% by mass of TMAH at 23° C. is preferably not more than 5 Å/sec, more preferably 0.05 to 5 Å/sec, and still more preferably 0.0005 to 5 Å/sec. When the dissolving speed is not more than 5 Å/sec, the exposed area is insoluble in an alkali developing solution and can form a resist. When the dissolving speed is not less than 0.0005 Å/sec, the resolution may be improved. This is guessed due to the fact that the micro surface site of the cyclic compound is dissolved to reduce LER. In addition, there is an effect of reducing the number of defects.

The radiation sensitive composition of the invention comprises preferably 1 to 80% by weight of the solid component and 20 to 99% by weight of the solvent, more preferably 1 to 50% by weight of the solid component and 50 to 99% by weight of the solvent, still more preferably 2 to 40% by weight of the solid component and 60 to 98% by weight of the solvent, and particularly preferably 2 to 10% by weight of the solid component and 90 to 98% by weight of the solvent. The content of the cyclic compound represented by the formula (1) is 50 to 99.999% by weight, preferably 65 to 80% by weight or more, and more preferably 60 to 70% by weight based on the total weight of the solid component. Within the above blending ratios, a high resolution is obtained and the line edge roughness becomes small.

The composition of the invention preferably contains one or more of acid generators (C) generating an acid directly or indirectly by the irradiation with a radiation selected from visible light, ultraviolet ray, excimer laser, electron beams, extreme ultraviolet ray (ELTV), X-ray and ion beams. The amount of the acid generator (C) used is preferably 0.001 to 50% by weight, more preferably 1 to 40% by weight, still more preferably 3 to 30% by weight, and particularly preferably 10 to 25% by weight based on the total weight of the solid component (total of the solid components of the cyclic compound, acid generator (C), acid crosslinking agent (G), acid-diffusion controller (E) and optionally used other component (F), the same being applied below). By using the composition within the above range is obtained a pattern profile with a high sensitivity and a low edge roughness. In the invention, methods of generating the acid are not limited as long as the acid is generated within the system. The use of excimer laser instead of ultraviolet ray such as g-rays and i-rays enables a finer processing. The use of electron beams, extreme ultraviolet ray, X-ray or ion beams as high-energy rays enables a further finer processing.

The acid generator (C) is preferable to be at least one selected from the group consisting of compounds represented by the following formulae (7-1) to (7-8).

[Chem. 21]

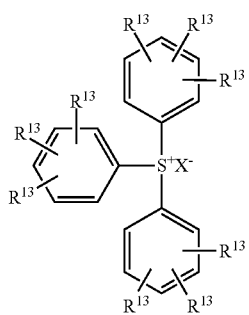

(7-1)

(in the formula (7-1), $R^{13}$(s) may be same or different and each is independently a hydrogen atom, a linear, branched or cyclic alkyl group, a linear, branched or cyclic alkoxyl group, a hydroxyl group or a halogen atom; and $X^-$ is a sulfonic acid ion or a halide ion having an alkyl group, an aryl group, a halogen-substituted alkyl group or a halogen-substituted aryl group).

The compound represented by the formula (7-1) is preferable to be at least one selected from the group consisting of triphenylsulfonium trifluoromethane sulfonate, triphenylsulfonium nonafluoro-n-butane sulfonate, diphenyltolylsulfonium nonafluoro-n-butane sulfonate, triphenylsulfonium perfluoro-n-octane sulfonate, diphenyl-4-methylphenylsulfonium trifluoromethane sulfonate, di-2,4,6-trimethylphenylsulfonium trifluoromethane sulfonate, diphenyl-4-t-butoxyphenylsulfonium trifluoromethane sulfonate, diphenyl-4-t-butoxyphenylsulfonium nonafluoro-n-butane sulfonate, diphenyl-4-hydroxyphenylsulfonium trifluoromethane sulfonate, bis(4-fluorophenyl)-4-hydroxyphenylsulfonium trifluoromethane sulfonate, diphenyl-4-hydroxyphenylsulfonium nonafluoro-n-butane sulfonate, bis(4-hydroxyphenyl)-phenylsulfonium trifluoromethane sulfonate, tri(4-methoxyphenyl)sulfonium trifluoromethane sulfonate, tri(4-fluorophenyl)sulfonium trifluoromethane sulfonate, triphenylsulfonium p-toluene sulfonate, triphenylsulfonium benzene sulfonate, diphenyl-2,4,6-trimethylphenyl-p-toluene sulfonate, diphenyl-2,4,6-trimethylphenylsulfonium-2-trifluoromethylbenzene sulfonate, diphenyl-2,4,6-trimethylphenylsulfonium-4-trifluoromethylbenzene sulfonate, diphenyl-2,4,6-trimethylphenylsulfonium-2,4-difluorobenzene sulfonate, diphenyl-2,4,6-trimethylphenylsulfonium hexafluorobenzene sulfonate, diphenylnaphthylsulfonium trifluoromethane sulfonate, diphenyl-4-hydroxyphenylsulfonium-p-toluene sulfonate, triphenylsulfonium 10-camphor sulfonate, diphenyl-4-hydroxyphenylsulfonium 10-camphor sulfonate, and cyclo (1,3-perfluoropropanedisulfon) imidate.

[Chem. 22]

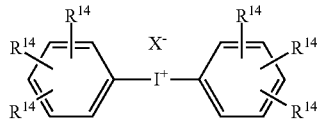

(7-2)

(in the formula (7-2), $R^{14}$(s) may be same or different and each is independently a hydrogen atom, a linear, branched or cyclic alkyl group, a linear, branched or cyclic alkoxy group, a hydroxyl group or a halogen atom, and $X^-$ is the same as described above).

The compound represented by the formula (7-2) is preferable to be at least one selected from the group consisting of bis(4-t-butylphenyl) iodonium trifluoromethane sulfonate, bis(4-t-butylphenyl) iodonium nonafluoro-n-butane sulfonate, bis(4-t-butylphenyl) iodonium perfluoro-n-octane sulfonate, bis(4-t-butylphenyl) iodonium p-toluene sulfonate, bis(4-t-butylphenyl) iodonium benzene sulfonate, bis(4-t-butylphenyl) iodonium-2-trifluoromethylbenzene sulfonate, bis(4-t-butylphenyl) iodonium-4-trifluoromethylbenzene sulfonate, bis(4-t-butylphenyl) iodonium-2,4-difluorobenzene sulfonate, bis(4-t-butylphenyl) iodonium hexafluorobenzene sulfonate, bis(4-t-butylphenyl) iodonium 10-camphor sulfonate, diphenyliodonium trifluoromethane sulfonate, diphenyliodonium nonafluoro-n-butane sulfonate, diphenyliodonium perfluoro-n-octane sulfonate, diphenyliodonium p-toluene sulfonate, diphenyliodonium benzene sulfonate, diphenyliodonium 10-camphor sulfonate, diphenyliodonium-2-trifluoromethylbenzene sulfonate, diphenyliodonium-4-trifluoromethylbenzene sulfonate, diphenyliodonium-2,4-difluorobenzene sulfonate, diphenyliodonium hexafluorobenzene sulfonate, di(4-trifluoromethylphenyl) iodonium trifluoromethane sulfonate, di(4-trifluoromethylphenyl) iodonium nonafluoro-n-butane sulfonate, di(4-trifluoromethylphenyl) iodonium perfluoro-n-octane sulfonate, di(4-trifluoromethylphenyl) iodonium p-toluene sulfonate, di(4-trifluoromethylphenyl) iodonium benzene sulfonate, and di(4-trifluoromethylphenyl) iodonium 10-camphor sulfonate.

[Chem. 23]

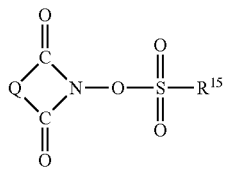

(7-3)

(in the formula (7-3), Q is an alkylene group, an arylene group or an alkoxylene group, and $R^{15}$ is an alkyl group, an aryl group, a halogen-substituted alkyl group or a halogen-substituted aryl group).

The compound represented by the formula (7-3) is preferable to be at least one selected from the group consisting of N-(trifluoromethylsulfonyloxy) succinimide, N-(trifluoromethylsulfonyloxy) phthalimide, N-(trifluoromethylsulfonyloxy) diphenylmaleimide, N-(trifluoromethylsulfonyloxy) bicyclo[2.2.1]hept-5-ene-2,3-dicarboxyimide, N-(trifluoromethylsulfonyloxy) naphthylimide, N-(10-camphorsulfonyloxy) succinimide, N-(10-camphorsulfonyloxy) phthalimide, N-(10-camphorsulfonyloxy) diphenylmaleimide, N-(10-camphorsulfonyloxy) bicyclo[2.2.1]hept-5-ene-2,3-dicarboxyimide, N-(10-camphorsulfonyloxy) naphthylimide, N-(n-octanesulfonyloxy) bicyclo[2.2.1]hept-5-ene-2,3-dicarboxyimide, N-(n-octanesulfonyloxy) naphthylimide, N-(p-toluenesulfonyloxy) bicyclo[2.2.1]hept-5-ene-2,3-dicarboxyimide, N-(p-toluenesulfonyloxy) naphthylimide, N-(2-trifluoromethylbenzenesulfonyloxy) bicyclo[2.2.1]hept-5-ene-2,3-dicarboxyimide, N-(2-trifluoromethylbenzenesulfonyloxy) naphthylimide, N-(4-trifluoromethylbenzenesulfonyloxy) bicyclo[2.2.1]hept-5-ene-2,3-dicarboxyimide, N-(4-trifluoromethylbenzenesulfonyloxy) naphthylimide, N-(perfluorobenzenesulfonyloxy) bicyclo[2.2.1]hept-5-ene-2,3-dicarboxyimide, N-(perfluorobenzenesulfonyloxy) naphthylimide, N-(1-naphthalenesulfonyloxy) bicyclo[2.2.1]hept-5-ene-2,3-dicarboxyimide, N-(1-naphthalenesulfonyloxy) naphthylimide, N-(nonafluoro-n-butanesulfonyloxy) bicyclo[2.2.1]hept-5-ene-2,3-dicarboxyimide, N-(nonafluoro-n-butanesulfonyloxy) naphthylimide, N-(perfluoro-n-octanesulfonyloxy) bicyclo[2.2.1]hept-5-ene-2,3-dicarboxyimide, and N-(perfluoro-n-octanesulfonyloxy) naphthylimide.

[Chem. 24]

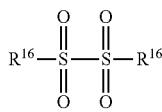

(7-4)

(in the formula (7-4), $R^{16}$(s) may be same or different and each is independently an optionally substituted linear, branched or cyclic alkyl group, an optionally substituted aryl group, an optionally substituted heteroaryl group or an optionally substituted aralkyl group).

The compound represented by the formula (7-4) is preferable to be at least one selected from the group consisting of diphenyl disulfone, di(4-methylphenyl)disulfone, dinaphthyl disulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

[Chem. 25]

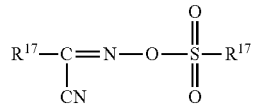

(7-5)

(in the formula (7-5), $R^{17}$(s) may be same or different and each is independently an optionally substituted linear, branched or cyclic alkyl group, an optionally substituted aryl group, an optionally substituted heteroaryl group or an optionally substituted aralkyl group).

The compound represented by the formula (7-5) is preferable to be at least one selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile and α-(methylsulfonyloxyimino)-4-bromophenylacetonitrile.

[Chem. 26]

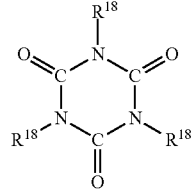

(7-6)

In the formula (7-6), $R^{18}$(s) may be same or different and each is independently a halogenated alkyl group having one or more chlorine atoms and one or more bromine atoms. The halogenated alkyl group preferably has 1 to 5 carbon atoms.

[Chem. 27]

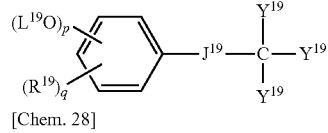

(7-7)

[Chem. 28]

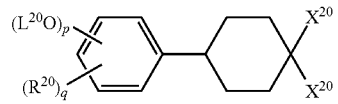

(7-8)

In the formulae (7-7) and (7-8), $R^{19}$ and $R^{20}$ are independently an alkyl group having a carbon number of 1 to 3 such as methyl group, ethyl group, n-propyl group, isopropyl group or the like; a cycloalkyl group such as cyclopentyl group, cyclohexyl group or the like; an alkoxyl group having a carbon number of 1 to 3 such as methoxy group, ethoxy group, propoxy group or the like; or an aryl group such as phenyl group, toluyl group, naphthyl group or the like, preferably an aryl group having a carbon number of 6 to 10. $L^{19}$ and $L^{20}$ are each independently an organic group having 1,2-naphthoquinonediazido group. As the organic group having 1,2-naphthoquinonediazido group may be preferably mentioned 1,2-diazidosulfonyl groups such as 1,2-naphthoquinonediazido-4-sulfonyl group, 1,2-naphthoquinonediazido-5-sulfonyl group, 1,2-naphthoquinonediazido-6-sulfonyl group and so on. Particularly, 1,2-naphthoquinonediazido-4-sulfonyl group and 1,2-naphthoquinonediazido-5-sulfonyl group are preferable, p is an integer of 1 to 3, and q is an integer of 0 to 4, and $1 \leq p+q \leq 5$. $J^{19}$ is a single bond, a polymethylene group having a carbon number of 1 to 4, a cycloalkylene group, phenylene group, a group represented by the following formula (7-7-1), carbonyl group, ester group, amide group or ether group; $Y^{19}$ is a hydrogen atom, an alkyl group or an aryl group; and $X^{20}$ is independently a group represented by the following formula (7-8-1).

[Chem. 29]

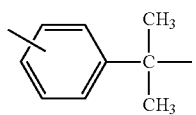

(7-7-1)

[Chem. 30]

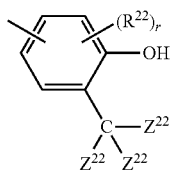

(7-8-1)

(in the formula (7-8-1), $Z^{22}$ is independently an alkyl group, a cycloalkyl group or an aryl group, $R^{22}$ is an alkyl group, a cycloalkyl group or an alkoxyl group, and r is an integer of 0 to 3.)

As another acid generator are mentioned bissulfonyldiazomethanes such as bis(p-toluenesulfonyl)diazomethane, bis (2,4-dimethylphenylsulfonyl) diazomethane, bis(tert-butylsulfonyl)diazomethane, bis(n-butylsulfonyl) diazomethane, bis(isobutylsulfonyl)diazomethane, bis(isopropylsulfonyl) diazomethane, bis(n-propylsulfonyl)diazomethane, bis(cyclohexylsulfonyl) diazomethane, bis(isopropylsulfonyl)diazomethane, 1,3-bis(cyclohexylsulfonylazomethylsulfonyl) propane, 1,4-bis(phenylsulfonylazomethylsulfonyl) butane, 1,6-bis(phenylsulfonylazomethylsulfonyl) hexane, 1,10-bis (cyclohexylsulfonylazomethylsulfonyl) decane and the like; halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, tris(2,3-dibromopropyl) isocyanurate and the like.

Among the above acid generators, an acid generator having an aromatic ring is preferable, and an acid generator represented by the formula (7-1) or (7-2) is more preferable. Still more preferred is an acid generator of the formula (7-1) or (7-2) wherein $X^-$ is sulfonic acid ion having an aryl group or a halogen-substituted aryl group, and particularly preferred is an acid generator wherein $X^-$ is sulfonic acid ion having an aryl group. Particularly, diphenyltrimethylphenylsulfonium p-toluenesulfonate, triphenylsulfonium p-toluenesulfonate, triphenylsulfonium trifluoromethanesulfonate, triphenylsulfonium nonafluoromethanesulfonate are preferable. The use of such an acid generator can reduce LER.

The acid generators (C) may be used alone or in a combination of two or more.

The radiation sensitive composition according to the invention is preferable to contain one or more of acid crosslinking agents (G). The acid crosslinking agent (G) means a compound capable of intramolecularly or intermolecularly crosslinking the cyclic compound (A) in the presence of an acid generated from the acid generator (C). As the acid crosslinking agent (G) can be mentioned, for example, compounds having one or more substituents of a crosslinking reactivity with the cyclic compound (A) (referred to as "crosslinkable substituent" hereinafter).

As a specific example of such a crosslinkable substituent are mentioned, for example, (i) a hydroxyalkyl group or a substituent derived therefrom such as hydroxy(C1-C6 alkyl), C1-C6 alkoxy(C1-C6 alkyl) group, acetoxy(C1-C6 alkyl) and the like; (ii) a carbonyl group or a substituent derived therefrom such as formyl group, carboxy(C1-C6 alkyl) and the like; (iii) a nitrogen group-containing substituent such as dimethylaminomethyl group, diethylaminomethyl group, dimethylolaminomethyl group, diethylolaminomethyl group, morpholinomethyl group and the like; (iv) a glycidyl group-containing substituent such as glycidyl ether group, glycidyl ester group, glycidylamino group and the like; (v) a substituent derived from an aromatic group such as C6-C12 alkyloxy(C1-C6 alkyl) group and C7-C13 aralkyloxy(C1-C6 alkyl) group, such as benzyloxymethyl group, benzoyloxymethyl group and the like; (vi) a polymerizable multiple bond-containing substituent such as vinyl group, isopropenyl group and the like. As the crosslinkable substituent of the acid crosslinking agent (G) in the invention, hydroxyalkyl group and alkoxyalkyl group are preferable, and particularly alkoxymethyl group is preferable.

As the acid crosslinking agent (G) having the crosslinkable substituent may be mentioned, for example, (i) methylol group-containing compounds such as a methylol group-containing melamine compound, a methylol group-containing benzoguanamine compound, a methylol group-containing urea compound, a methylol group-containing glycoluril compound, a methylol group-containing phenol compound and the like; (ii) alkoxyalkyl group-containing compounds such as an alkoxyalkyl group-containing melamine compound, an alkoxyalkyl group-containing benzoguanamine compound, an alkoxyalkyl group-containing urea compound, an alkoxyalkyl group-containing glycoluril compound, an alkoxyalkyl group-containing phenol compound and the like; (iii) carboxymethyl group-containing compounds such as a carboxymethyl group-containing melamine compound, a carboxymethyl group-containing benzoguanamine compound, a carboxymethyl group-containing urea compound, a carboxymethyl group-containing glycoluril compound, a carboxymethyl group-containing phenol compound and the like; and (iv) epoxy compounds such as a bisphenol A-based epoxy compound, a bisphenol F-based epoxy compound, a bisphenol S-based epoxy compound, a novolak resin-based epoxy compound, a resol resin-based epoxy compound, a poly(hydroxystyrene)-based epoxy compound and the like.

As the acid crosslinking agent (G) can be further used a compound having a phenolic hydroxyl group as well as a compound or resin having a crosslinkability given by introducing the crosslinkable substituent into an acidic functional group of an alkali-soluble resin. In this case, the introduction ratio of the crosslinkable group is controlled usually 5 to 100 mol %, preferably 10 to 60 mol %, and still more preferably 15 to 40 mol % based on the total acidic functional groups in the compound having a phenolic hydroxyl group or the alkali-soluble resin. When the ratio is within the above range, the crosslinking reaction proceeds sufficiently, and hence the lowering of residual film percentage, and the swelling and meandering of patterns are avoided.

In the radiation sensitive composition according to the invention, the acid crosslinking agent (G) is preferable to be an alkoxyalkylated urea compound or its resin, or an alkoxyalkylated glycoluril compound or its resin. As the particularly preferred acid crosslinking agents (G) can be mentioned compounds represented by the following formulae (8-1) to (8-3) and alkoxymethylated melamine compounds (acid crosslinking agent (G1)).

[Chem. 31]

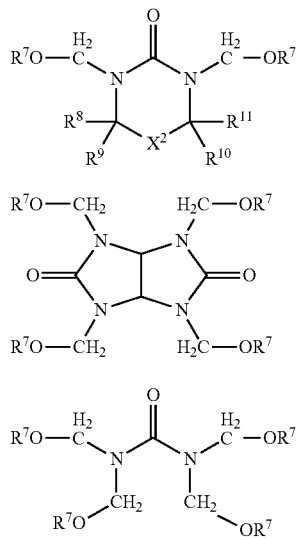

(wherein $R^7$ is independently a hydrogen atom, an alkyl group or an acyl group; $R^8$ to $R^{11}$ are independently a hydrogen atom, hydroxyl group, an alkyl group or an alkoxyl group; and $X^2$ is a single bond, methylene group or oxygen atom.)

In the formulae (8-1) to (8-3), $R^7$ is preferably a hydrogen atom, an alkyl group having a carbon number of 1 to 6 or an acyl group having a carbon number of 2 to 6. As the alkyl group having a carbon number of 1 to 6 is more preferable an alkyl group having a carbon number of 1 to 3, which includes, for example, methyl group, ethyl group and propyl group. As the acyl group having a carbon number of 2 to 6 is more preferable an acyl group having a carbon number of 2 to 4, which includes, for example, acetyl group and propionyl group. $R^8$ to $R^{11}$ in the formula (8) are preferably a hydrogen atom, hydroxyl group, an alkyl group having a carbon number of 1 to 6, or an alkoxyl group having a carbon number of 1 to 6. As the alkyl group having a carbon number of 1 to 6 is more preferable an alkyl group having a carbon number of 1 to 3, which includes, for example, methyl group, ethyl group and propyl group. As the alkoxyl group having a carbon number of 1 to 6 is more preferable an alkoxyl group having a carbon number of 1 to 3, which includes, for example, methoxy group, ethoxy group and propoxy group. $X^2$ represents a single bond, methylene group or oxygen atom and is preferable to be a single bond or methylene group. Moreover, $R^7$ to $R^{11}$ and $X^2$ may further have a substituent, for example, an alkyl group such as methyl group, ethyl group or the like; an alkoxyl group such as methoxy group, ethoxy group or the like; hydroxyl group, or a halogen atom in the groups exemplified above. Plural $R^7$, and $R^8$ to $R^{11}$ may be same or different.

As the compound represented by the formula (8-1) may be specifically mentioned, for example, the following compounds.

[Chem. 32]

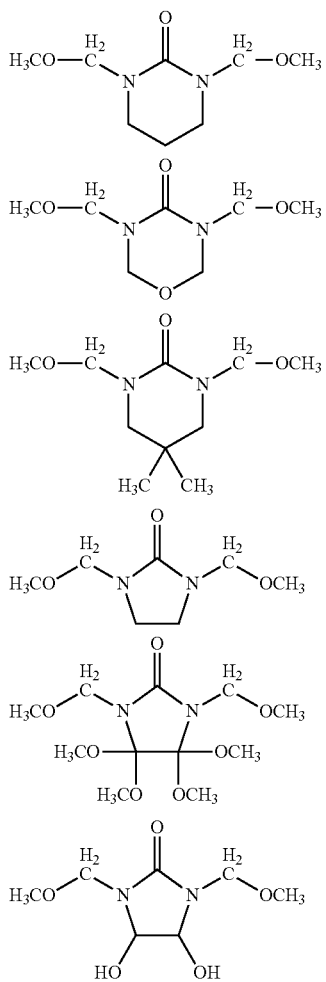

As the compound represented by the formula (8-2) are specifically mentioned, for example, N,N,N,N-tetra(methoxymethyl)glycoluril, N,N,N,N-tetra(ethoxymethyl) glycoluril, N,N,N,N-tetra(n-propoxymethyl)glycoluril, N,N,N,N-tetra(isopropoxymethyl)glycoluril, N,N,N,N-tetra(n-butoxymethyl) glycoluril, N,N,N,N-tetra(t-butoxymethyl) glycoluril and the like. Among them, N,N,N,N-tetra(methoxymethyl)glycoluril is particularly preferred.

As the compound represented by the formula (8-3) are specifically mentioned, for example, the following compounds.

[Chem. 33]

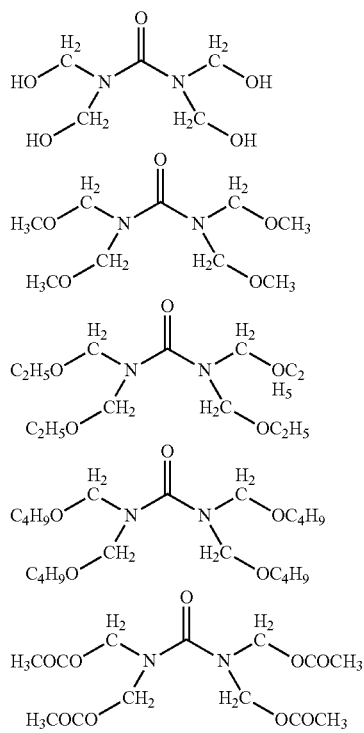

As the alkoxymethylated melamine compound are specifically mentioned, for example, N,N,N,N,N,N-hexa(methoxymethyl) melamine, N,N,N,N,N,N-hexa(ethoxymethyl) melamine, N,N,N,N,N,N-hexa(n-propoxymethyl) melamine, N,N,N,N,N,N-hexa(isopropoxymethyl) melamine, N,N,N,N,N,N-hexa(n-butoxymethyl) melamine, N,N,N,N,N,N-hexa(t-butoxymethyl) melamine and the like. Among them, N,N,N,N,N,N-hexa(methoxymethyl) melamine is particularly preferable.

The acid crosslinking agent (G1) is obtained, for example, by condensation-reacting a urea compound or a glycoluril compound with formalin to introduce methylol group therein, etherifying with a lower alcohol such as methyl alcohol, ethyl alcohol, propyl alcohol, butyl alcohol or the like and then cooling the reaction liquid to recover the precipitated compound or resin. Also, the acid crosslinking agent (G1) can be available as a commercial product such as CYMEL (tradename, manufactured by Mitsui Cyanamid, Inc.) and Nikalac (manufactured by Sanwa Chemical Co., Ltd.).

As another preferable acid crosslinking agent (G) may be mentioned a phenol derivative (acid crosslinking agent (G2)) having in its molecule 1 to 6-benzene rings and two or more hydroxyalkyl groups and/or alkoxyalkyl groups in total wherein the hydroxyalkyl groups and/or alkoxyalkyl groups are bonded to any of the benzene rings. Preferably mentioned is a phenol derivative having a molecular weight of not more than 1500 and having in its molecule 1 to 6 benzene rings and two or more hydroxyalkyl groups and/or alkoxyalkyl groups in total wherein the hydroxyalkyl groups and/or alkoxyalkyl groups are bonded to any one or more of the benzene rings.

As the hydroxyalkyl group to be bonded to the benzene ring are preferable those having a carbon number of 1 to 6 such as hydroxymethyl group, 2-hydroxyethyl group, 2-hydroxy-1-propyl group and so on. As the alkoxyalkyl group to be bonded to the benzene ring are preferable those having a carbon number of 2 to 6. Specifically, methoxymethyl group, ethoxymethyl group, n-propoxymethyl group, isopropoxymethyl group, n-butoxymethyl group, isobutoxymethyl group, sec-butoxymethyl group, t-butoxymethyl group, 2-methoxyethyl group and 2-methoxy-1-propyl group are preferable.

Among those phenol derivatives, particularly preferred ones are listed below.

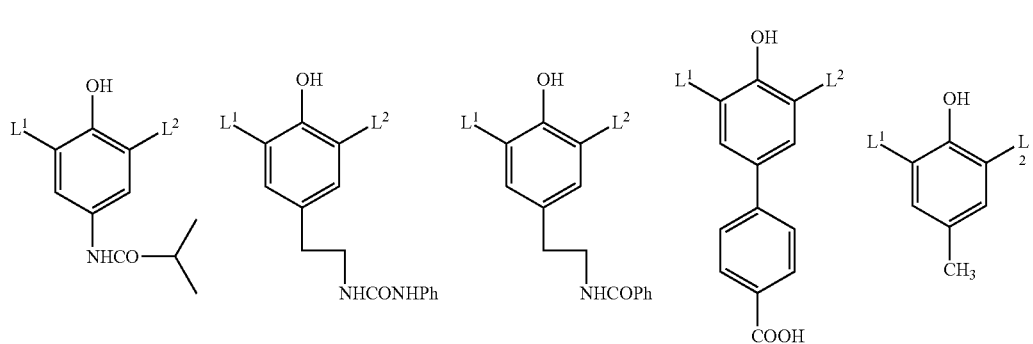

[Chem. 34]

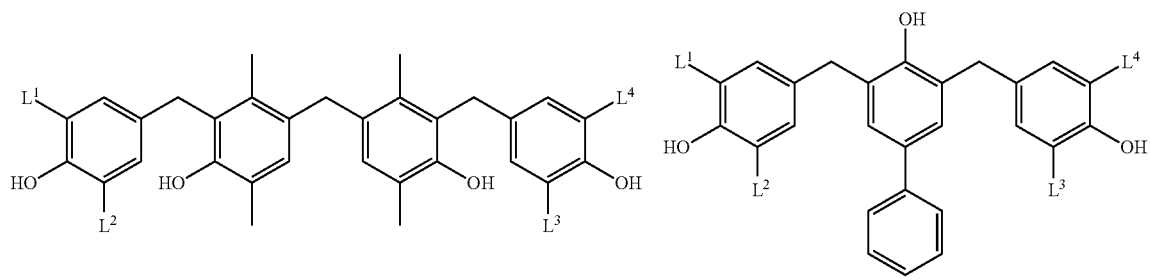

[Chem. 35]

-continued
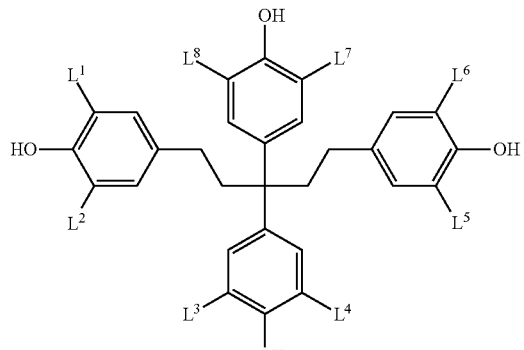
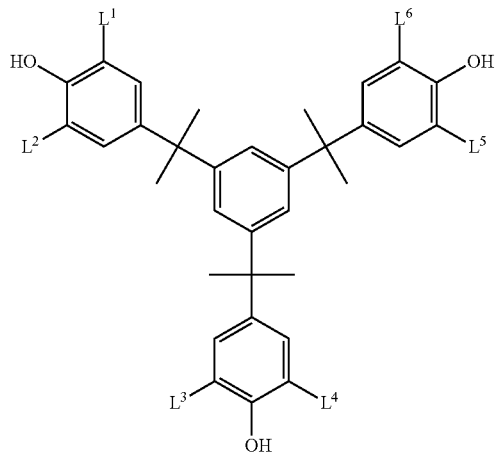
[Chem. 36]
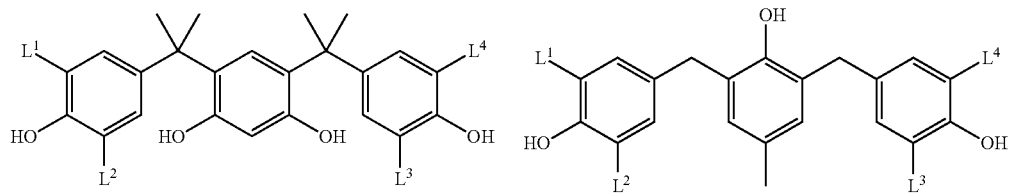
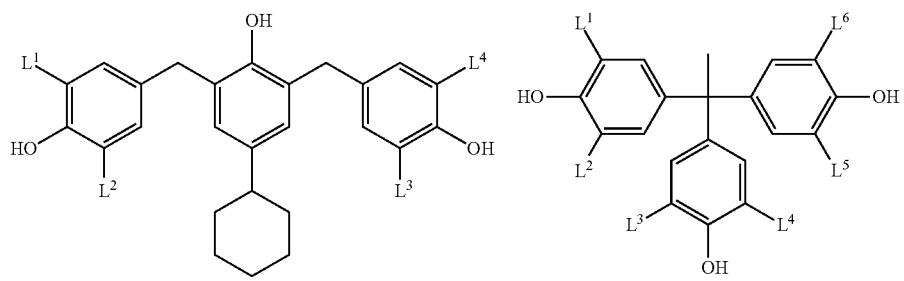
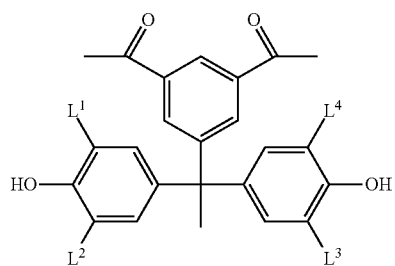
[Chem. 37]
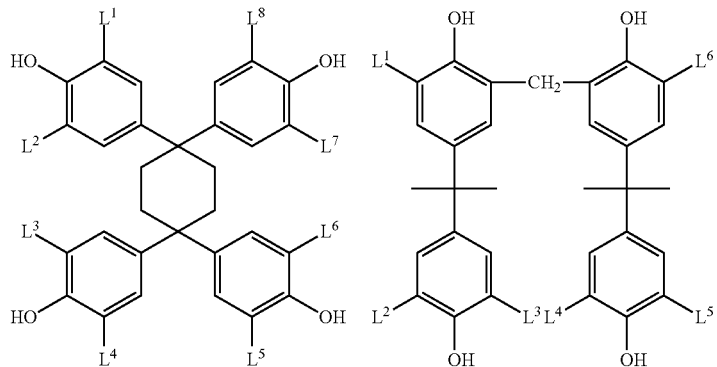

-continued
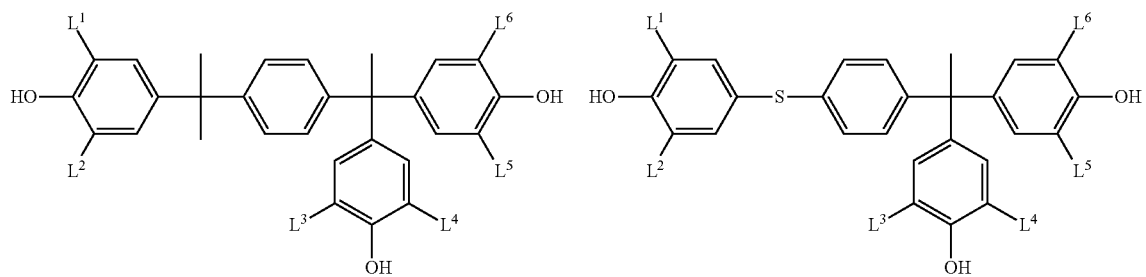
[Chem. 38]
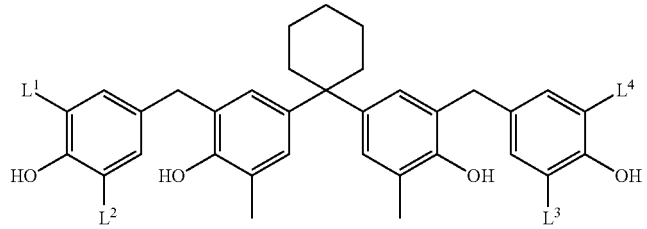
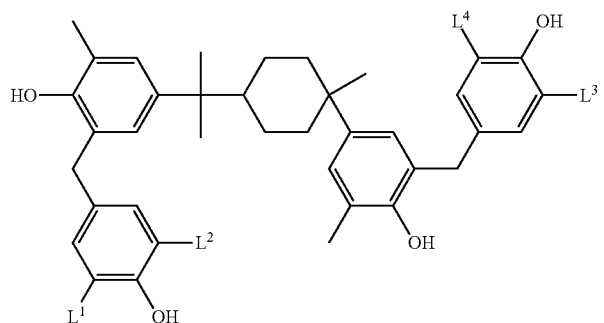
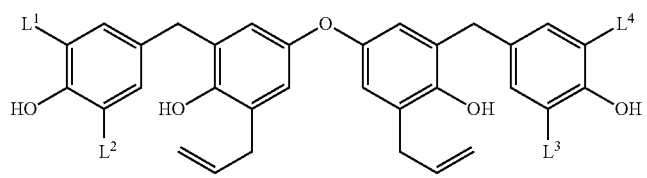
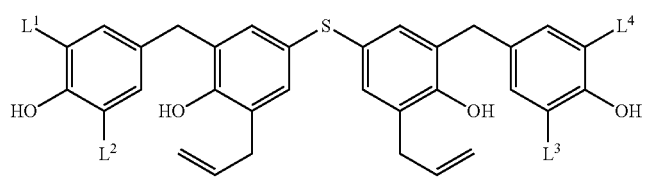
[Chem. 39]
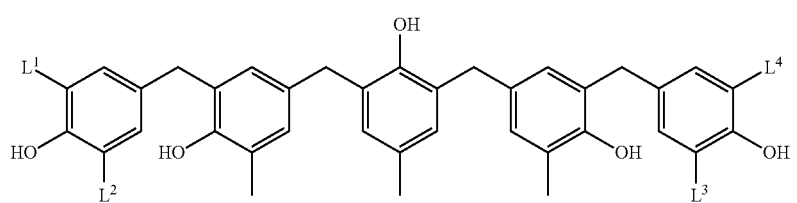

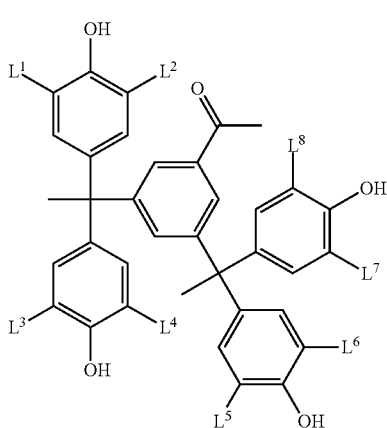

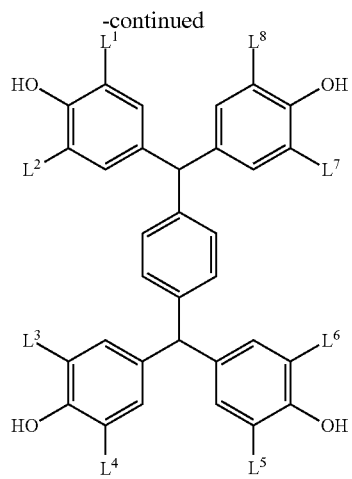

In the above formulae, $L^1$ to $L^8$ may be same or different and represent each independently hydroxymethyl group, methoxymethyl group or ethoxymethyl group. The phenol derivative having a hydroxymethyl group can be obtained by reacting a corresponding phenol compound having no hydroxymethyl group (compound of the above formulae in which $L^1$ to $L^8$ are each hydrogen atom) with formaldehyde in the presence of a base catalyst. In this case, the reaction is preferably carried out at a reaction temperature of not higher than 60° C. for preventing resinification or gelatinization. Concretely, it may be synthesized by a method described in JP-A-H06-282067, JP-A-H07-64285 or the like.

The phenol derivative having an alkoxymethyl group can be obtained by reacting a corresponding phenol derivative having a hydroxymethyl group with an alcohol in the presence of an acid catalyst. In this case, the reaction is preferably carried out at a reaction temperature of not higher than 100° C. for preventing resinification or gelatinization. Concretely, it may be synthesized by a method described in EP 632003A1 or the like.

The thus synthesized phenol derivative having hydroxymethyl group and/or alkoxymethyl group is preferable in view of storage stability, and the phenol derivative having alkoxymethyl group is particularly preferable from the viewpoint of storage stability. The acid crosslinking agents (G2) may be used alone or in a combination of two or more.

As the other preferable acid crosslinking agent (G) may be mentioned compounds having at least one α-hydroxyisopropyl group (acid crosslinking agent (G3)). Such a compound is not particularly limited in their structure as long as it have α-hydroxyisopropyl group. Also, hydrogen atom of hydroxyl group in the above α-hydroxyisopropyl group may be replaced by one or more acid-dissociable groups (R—COO— group, R—SO$_2$— group and the like, wherein R represents a substituent selected from the group consisting of a linear hydrocarbon group having a carbon number of 1 to 12, a cyclic hydrocarbon group having a carbon number of 3 to 12, an alkoxy group having a carbon number of 1 to 12, a 1-branched alkyl group having a carbon number of 3 to 12 and an aromatic hydrocarbon group having a carbon number of 6 to 12). As the compound having α-hydroxyisopropyl group are mentioned, for example, one or more of substituted or non-substituted aromatic compounds, diphenyl compounds, naphthalene compounds, furan compounds and the like, each having at least one α-hydroxyisopropyl group. Specifically, there are mentioned, for example, compounds represented by the following general formula (9-1) (hereinafter referred to as "benzene series compound (1)"), compounds represented by the following general formula (9-2) (hereinafter referred to as "diphenyl series compound (2)"), compounds represented by the following general formula (9-3) (hereinafter referred to as "naphthalene series compound (3)"), compounds represented by the following general formula (9-4) (hereinafter referred to as "furan series compound (4)") and the like.

[Chem. 40]

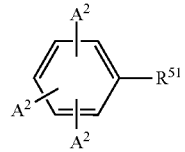

(9-1)

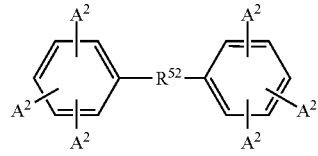

(9-2)

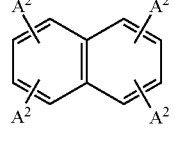

(9-3)

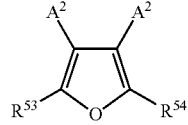

(9-4)

In the general formulae (9-1) to (9-4), each $A^2$ represents independently an α-hydroxyisopropyl group or a hydrogen atom, and at least one $A^2$ is α-hydroxyisopropyl group. In the general formula (9-1), $R^{51}$ represents a hydrogen atom, hydroxyl group, a linear or branched alkylcarbonyl group having a carbon number of 2 to 6, or a linear or branched alkoxycarbonyl group having a carbon number of 2 to 6. In the general formula (9-2), $R^{52}$ represents a single bond, a linear or branched alkylene group having a carbon number of 1 to 5, —O—, —CO—, or —COO—. In the general formula (9-4), $R^{53}$ and $R^{54}$ represent each independently a hydrogen atom or a linear or branched alkyl group having a carbon number of 1 to 6.

As the benzene series compound (1) are specifically mentioned, for example, α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, 1,3,5-tris(α-hydroxyisopropyl)benzene and the like; α-hydroxyisopropylphenols such as 3-α-hydroxyisopropylphenol, 4-α-hydroxyisopropylphenol, 3,5-bis(α-hydroxyisopropyl)phenol, 2,4,6-tris(α-hydroxyisopropyl)phenol and the like; α-hydroxyisopropylphenyl alkyl ketones such as 3-α-hydroxyisopropylphenyl methyl ketone, 4-α-hydroxyisopropylphenyl methyl ketone, 4-α-hydroxyisopropylphenyl ethyl ketone, 4-α-hydroxyisopropylphenyl n-propyl ketone, 4-α-hydroxyisopropylphenyl isopropyl ketone, 4-α-hydroxyisopropylphenyl n-butyl ketone, 4-α-hydroxyisopropylphenyl t-butyl ketone, 4-α-hydroxyisopropylphenyl n-pentyl ketone, 3,5-bis(α-hydroxyisopropyl)phenyl methyl ketone, 3,5-bis(α-hydroxyisopropyl)phenyl ethyl ketone, 2,4,6-tris(α-hydroxyisopropyl)phenyl methyl ketone and the like; alkyl 4-α-hydroxyisopropylbenzoates such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, methyl 2,4,6-tris(α-hydroxyisopropyl)benzoate and the like.

As the diphenyl series compound (2) are specifically mentioned, for example, α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6-tetrakis(α-hydroxyisopropyl)biphenyl, 2,4,4',6-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl, 2,2',4,4',6,6'-hexakis(α-hydroxyisopropyl)biphenyl and the like; α-hydroxyisopropyldiphenyl alkanes such as 3-α-hydroxyisopropyldiphenyl methane, 4-α-hydroxyisopropyldiphenyl methane, 1-(4-α-hydroxyisopropylphenyl)-2-phenyl ethane, 1-(4-α-hydroxyisopropylphenyl)-2-phenyl propane, 2-(4-α-hydroxyisopropylphenyl)-2-phenyl propane, 1-(4-α-hydroxyisopropylphenyl)-3-phenyl propane, 1-(4-α-hydroxyisopropylphenyl)-4-phenyl butane, 1-(4-α-hydroxyisopropylphenyl)-5-phenyl pentane, 3,5-bis(α-hydroxyisopropyl)diphenyl methane, 3,3'-bis(α-hydroxyisopropyl)diphenyl methane, 3,4'-bis(α-hydroxyisopropyl)diphenyl methane, 4,4'-bis(α-hydroxyisopropyl)diphenyl methane, 1,2-bis(4-α-hydroxyisopropylphenyl) ethane, 1,2-bis(4-α-hydroxypropylphenyl) propane, 2,2-bis(4-α-hydroxypropylphenyl) propane, 1,3-bis(4-α-hydroxypropylphenyl) propane, 2,4,6-tris(α-hydroxyisopropyl)diphenyl methane, 3,3',5-tris(α-hydroxyisopropyl)diphenyl methane, 3,4',5-tris(α-hydroxyisopropyl)diphenyl methane, 2,3',4,6-tetrakis(α-hydroxyisopropyl)diphenyl methane, 2,4,4',6-tetrakis(α-hydroxyisopropyl)diphenyl methane, 3,3',5,5'-tetrakis(α-hydroxyisopropyl)diphenyl methane, 2,3',4,5',6-pentakis(α-hydroxyisopropyl)diphenyl methane, 2,2',4,4',6,6'-hexakis(α-hydroxyisopropyl)diphenyl methane and the like; α-hydroxyisopropyldiphenyl ethers such as 3-α-hydroxyisopropyldiphenyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4',6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, 2,2',4,4',6,6'-hexakis(α-hydroxyisopropyl)diphenyl ether and the like; α-hydroxyisopropyldiphenyl ketones such as 3-α-hydroxyisopropyldiphenyl ketone, 4-α-hydroxyisopropyldiphenyl ketone, 3,5-bis(α-hydroxyisopropyl)diphenyl ketone, 3,3'-bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl)diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, 2,2',4,4',6,6'-hexakis(α-hydroxyisopropyl)diphenyl ketone and the like; phenyl α-hydroxyisopropylbenzoates such as phenyl 3-α-hydroxyisopropylbenzoate, phenyl 4-α-hydroxyisopropylbenzoate, 3-α-hydroxyisopropylphenyl benzoate, 4-α-hydroxyisopropylphenyl benzoate, phenyl 3,5-bis(α-hydroxyisopropyl)benzoate, 3-α-hydroxyisopropylphenyl 3-α-hydroxyisopropylbenzoate, 4-α-hydroxyisopropylphenyl 3-α-hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α-hydroxyisopropyl)phenyl benzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris(α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate and the like.

Furthermore, as the naphthalene series compound (3) are specifically mentioned, for example, 1-(α-hydroxyisopropyl) naphthalene, 2-α-hydroxyisopropyl) naphthalene, 1,3-bis(α-hydroxyisopropyl) naphthalene, 1,4-bis(α-hydroxyisopropyl) naphthalene, 1,5-bis(α-hydroxyisopropyl) naphthalene, 1,6-bis(α-hydroxyisopropyl) naphthalene, 1,7-bis(α-hydroxyisopropyl) naphthalene, 2,6-bis(α-hydroxyisopropyl) naphthalene, 2,7-bis(α-hydroxyisopropyl) naphthalene, 1,3,5-tris(α-hydroxyisopropyl) naphthalene, 1,3,6-tris(α-hydroxyisopropyl) naphthalene, 1,3,7-tris(α-hydroxyisopropyl) naphthalene, 1,4,6-tris(α-hydroxyisopropyl)

naphthalene, 1,4,7-tris(α-hydroxyisopropyl) naphthalene, 1,3,5,7-tetrakis(α-hydroxyisopropyl) naphthalene and so on.

As the furan series compound (4) are specifically mentioned, for example, 3-(α-hydroxyisopropyl) furan, 2-methyl-3-(α-hydroxyisopropyl) furan, 2-methyl-4-(α-hydroxyisopropyl) furan, 2-ethyl-4-(α-hydroxyisopropyl) furan, 2-n-propyl-4-(α-hydroxyisopropyl) furan, 2-isopropyl-4-(α-hydroxyisopropyl) furan, 2-n-butyl-4-(α-hydroxyisopropyl) furan, 2-t-butyl-4-(α-hydroxyisopropyl) furan, 2-n-pentyl-4-(α-hydroxyisopropyl) furan, 2,5-dimethyl-3-α-hydroxyisopropyl) furan, 2,5-diethyl-3-(α-hydroxyisopropyl) furan, 3,4-bis(α-hydroxyisopropyl) furan, 2,5-dimethyl-3,4-bis(α-hydroxyisopropyl) furan, 2,5-diethyl-3,4-bis(α-hydroxyisopropyl) furan and so on.

As the acid crosslinking agent (G3) is preferable the compound having two or more free α-hydroxyisopropyl groups. Further, the benzene series compounds having two or more α-hydroxyisopropyl groups (1), the diphenyl series compounds having two or more α-hydroxyisopropyl groups (2) and the naphthalene series compounds having two or more α-hydroxyisopropyl groups (3) are preferable, and particularly α-hydroxyisopropylbiphenyl compounds having two or more α-hydroxyisopropyl groups and naphthalene series compounds having two or more α-hydroxyisopropyl groups (3) are preferable.

The above acid crosslinking agent (G3) can be usually obtained by a method in which an acetyl group-containing compound such as 1,3-diacetylbenzene is methylated by reacting with a Grignard reagent such as $CH_3MgBr$ and then hydrolyzed, or a method in which an isopropyl group-containing compound such as 1,3-diisopropylbenzene is oxidized with oxygen or the like to produce a peroxide and then the peroxide is reduced.

In the invention, the blending ratio of the acid crosslinking agent (G) is 1 to 100 parts by weight, preferably 1 to 80 parts by weight, still more preferably 2 to 60 parts by weight, and particularly preferably 4 to 40 parts by weight based on 100 parts by weight of the cyclic compound represented by the formula (1). If the blending ratio of the acid crosslinking agent (G) is not less than 0.5 part by weight, the effect of controlling the solubility of the resist film in an alkali developing solution is enhanced to prevent the lowering of residual film percentage and the swelling or meandering of the patterns. While, if the blending ratio is not more than 50 parts by weight, the deterioration of the heat resistance as the resist can be suppressed.

The blending ratio of at least one compound selected from the acid crosslinking agent (G1), acid crosslinking agent (G2) and acid crosslinking agent (G3) in the acid crosslinking agent (G) is not particularly limited, and may be varied depending upon the kind of substrate to be used in the formation of resist patterns.

In the total of the acid crosslinking agents, the alkoxymethylated melamine compound and/or the compounds represented by the formulae (9-1) to (9-3) is preferable to be 50 to 99% by weight, preferably 60 to 99% by weight, more preferably 70 to 98% by weight, and still more preferably 80 to 97% by weight. When the alkoxymethylated melamine compound and/or the compounds represented by the formulae (9-1) to (9-3) is not less than 50% by weight of the total of the acid crosslinking agents, the resolution can be preferably improved, while when it is not more than 99% by weight, the cross section of the patterns is easily made into a rectangular shape.

In the invention, the radiation sensitive composition may contain an acid-diffusion controller (E) having a function of suppressing diffusion of an acid generated from the acid generator through the irradiation of radiation into the resist film to prevent undesirable chemical reaction in unexposed areas. By using the acid-diffusion controller (E) is improved the storage stability of the radiation sensitive composition. In addition, the resolution is improved and the change in line width of resist patterns due to the change in the process time-delay before the irradiation of electron beams and the change in the process time-delay after the irradiation of electron beams can be suppressed, and hence the processing stability becomes very excellent. As the acid-diffusion controller (E) are mentioned basic compounds capable of decomposing by the irradiation of electron beams such as nitrogen atom-containing basic compounds, basic sulfonium compounds, basic iodonium compounds and the like. The acid-diffusion controllers may be used alone or in a combination of two or more.

As the acid-diffusion controller are mentioned, for example, nitrogen-containing organic compounds, basic compounds decomposing upon the exposure and so on. As the nitrogen-containing organic compound, mention may be made of, for example, compounds represented by the following general formula (10) (hereinafter referred to as "nitrogen-containing compound (1)"):

[Chem. 41]

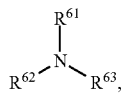

(10)

diamino compounds having two nitrogen atoms in its molecule (hereinafter referred to as "nitrogen-containing compound (II)"), polyamino compounds or polymers having three or more nitrogen atoms (hereinafter referred to as "nitrogen-containing compound (III)"), amido group-containing compounds, urea compounds, nitrogen-containing heterocyclic compounds and the like. Moreover, the above acid-diffusion controllers may be used alone or in a combination of two or more.

In the general formula (10), $R^{61}$, $R^{62}$ and $R^{63}$ represent each independently a hydrogen atom, a linear, branched or cyclic alkyl group, an aryl group or an aralkyl group. The alkyl group, aryl group or aralkyl group may be non-substituted or may be substituted by another functional group such as hydroxyl group or the like. As the linear, branched or cyclic alkyl group are mentioned, for example, those having a carbon number of 1 to 15, preferably 1 to 10, which include specifically methyl group, ethyl group, n-propyl group, isopropyl group, n-butyl group, isobutyl group, sec-butyl group, t-butyl group, n-pentyl group, neopentyl group, n-hexyl group, thexyl group, n-heptyl group, n-octyl group, n-ethylhexyl group, n-nonyl group, n-decyl group and the like. As the aryl group are mentioned those having a carbon number of 6 to 12, which include specifically phenyl group, tolyl group, xylyl group, cumenyl group, 1-naphthyl group and the like. As the aralkyl group are mentioned those having a carbon number of 7 to 19, preferably 7 to 13, which include specifically benzyl group, α-methylbenzyl group, phenethyl group, naphthylmethyl group and the like.

As the nitrogen-containing compound (I) are specifically mentioned, for example, mono(cyclo)alkyl amines such as n-hexylamine, n-heptylamine, n-octylamine, n-nonylamine, n-decylamine, n-dodecylamine, cyclohexylamine and the like; di(cyclo)alkyl amines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, dicyclohexylamine and the like; tri(cyclo)alkyl amines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, tricyclohexylamine and the like;

alkanol amines such as monoethanolamine, diethanolamine, triethanolamine and the like; aromatic amines such as aniline, N-methylaniline, N,N-dimethylaniline, 2-methylaniline, 3-methylaniline, 4-methylaniline, 4-nitroaniline, diphenylamine, triphenylamine, 1-naphthylamine and the like.

As the nitrogen-containing compound (II) are specifically mentioned, for example, ethylene diamine, N,N,N',N'-tetramethylethylene diamine, N,N,N',N'-tetrakis(2-hydroxypropyl)ethylene diamine, tetramethylene diamine, hexamethylene diamine, 4,4'-diaminodiphenylmethane, 4,4'-diaminodiphenyl ether, 4,4'-diaminobenzophenone, 4,4'-diaminodiphenylamine, 2,2-bis(4-aminophenyl) propane, 2-(3-aminophenyl)-2-(4-aminophenyl) propane, 2-(4-aminophenyl)-2-(3-hydroxyphenyl) propane, 2-(4-aminophenyl)-2-(4-hydroxyphenyl) propane, 1,4-bis[1-(4-aminophenyl)-1-methylethyl]benzene, 1,3-bis[1-(4-aminophenyl)-1-methylethyl]benzene and the like.

As the nitrogen-containing compound (III) are specifically mentioned, for example, polyethyleneimine, polyallylamine, polymer of N-(2-dimethylaminoethyl)acrylamide and the like.

As the amido group-containing compound are specifically mentioned, for example, formamide, N-methylformamide, N,N-dimethylformamide, acetamide, N-methylacetamide, N,N-dimethylacetamide, propionamide, benzamide, pyrrolidone, N-methylpyrrolidone and the like.

As the urea compound are specifically mentioned, for example, urea, methylurea, 1,1-dimethylurea, 1,3-dimethylurea, 1,1,3,3-tetramethylurea, 1,3-diphenylurea, tri-n-butylthiourea and the like.

As the nitrogen-containing heterocyclic compound are specifically mentioned, for example, imidazoles such as imidazole, benzimidazole, 4-methylimidazole, 4-methyl-2-phenylimidazole, 2-phenylbenzimidazole and the like; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinic amide, quinoline, 8-oxyquinoline, acridine and the like; and pyrazine, pyrazole, pyridazine, quinoxaline, purine, pyrrolidine, piperidine, morpholine, 4-methylmorpholine, piperazine, 1,4-dimethylpiperazine, 1,4-diazabicyclo[2.2.2]octane and the like.

As the basic compound decomposing upon the exposure are mentioned, for example, sulfonium compounds represented by the following general formula (11-1):

[Chem. 42]

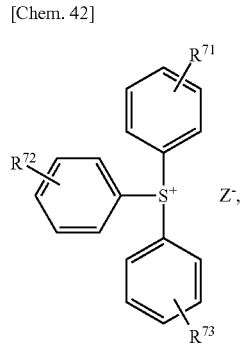

(11-1)

and iodonium compounds represented by the following general formula (11-2):

[Chem. 43]

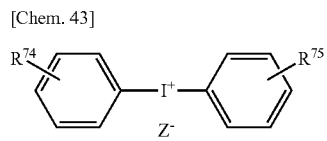

(11-2)

and the like.

In the general formulae (11-1) and (11-2), $R^{71}$, $R^{72}$, $R^{73}$, $R^{74}$ and $R^{75}$ represent each independently a hydrogen atom, an alkyl group having a carbon number of 1 to 6, an alkoxyl group having a carbon number of 1 to 6, hydroxyl group or a halogen atom. $Z^-$ represents $HO^-$, $R—COO^-$ (wherein R represents an alkyl group having a carbon number of 1 to 6, an aryl group having a carbon number of 1 to 6 or an alkaryl group having a carbon number of 1 to 6) or an anion represented by the following general formula (11-3).

[Chem. 44]

(11-3)

As the basic compound decomposing upon the exposure are specifically mentioned, for example, triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl) iodonium hydroxide, bis(4-t-butylphenyl) iodonium acetate, bis(4-t-butylphenyl) iodonium hydroxide, bis(4-t-butylphenyl) iodonium acetate, bis(4-t-butylphenyl) iodonium salicylate, 4-t-butylphenyl-4-hydroxyphenyliodonium hydroxide, 4-t-butylphenyl-4-hydroxyphenyliodonium acetate and 4-t-butylphenyl-4-hydroxyphenyliodonium salicylate and the like.

The blending amount of the acid-diffusion controller (E) is preferably 0.001 to 50% by weight, more preferably 0.001 to 10% by weight, still more preferably 0.001 to 5% by weight, and particularly preferably 0.001 to 3% by weight. Within the above ranges, the lowering of resolution and the deterioration of pattern profiles, dimension accuracy and the like can be prevented. In addition, the upper profile of the pattern is never deteriorated even if the process-time delay from the irradiation of radiation to the heating after the irradiation is prolonged. If the blending amount is not more than 10% by weight, the deterioration of sensitivity, developability of the unexposed area and the like can be prevented. Further, the use of such an acid-diffusion controller improves the storage stability of the radiation sensitive composition, improves the resolution and can suppress the change in line width of resist patterns due to the change in the process-time delay before the irradiation of electron beams or the change in the process-time delay after the irradiation of electron beams, and hence the processing stability becomes very excellent.

The radiation sensitive composition according to the invention may be added with one or more of various additives such as a dissolution promoter, a solubility controller, a sensitizer, a surfactant, an organic carboxylic acid or a phosphorus oxoacid or its derivative and so on as other component (F), if necessary, within a range not damaging the object of the invention.

[1] Dissolution Promoter

A low molecular weight dissolution promoter is a component having such an action that when the solubility of the cyclic compound in the developing solutions such as alkali or the like is too low, the solubility is enhanced to properly increase the dissolving speed of the cyclic compound during developing, and may be used within a range not damaging the effect of the invention. As the dissolution promoter are mentioned, for example, low-molecular weight phenolic compounds such as bisphenols, tris(hydroxyphenyl)methane and so on. These dissolution promoters may be used alone or in a combination of two or more. The blending amount of the dissolution promoter is properly adjusted depending upon the kind of the cyclic compound to be used, but is 0 to 100 parts by weight, preferably 0 to 30 parts by weight, more preferably 0 to 10 parts by weight, and still more preferably 0 to 2 parts by weight per 100 parts by weight of the cyclic compound represented by the formula (1).

[2] Solubility Controller

The solubility controller is a component having such an action that when the solubility of the cyclic compound represented by the formula (1) in the developing solution is too high, the solubility of the cyclic compound is controlled to properly reduce the dissolving speed during developing. It is preferred that the solubility controller is not chemically changed in the steps of baking the resist film, irradiating radiation and developing.

As the solubility controller may be mentioned, for example, aromatic hydrocarbons such as naphthalene, phenanthrene, anthracene, acenaphthene and the like; ketones such as acetophenone, benzophenone, phenyl naphthyl ketone and the like; sulfones such as methyl phenyl sulfone, diphenyl sulfone, dinaphthyl sulfone and the like. These solubility controllers may be used alone or in a combination of two or more.

The blending amount of the solubility controller is properly adjusted depending upon the kind of the cyclic compound to be used, but is 0 to 100 parts by weight, preferably 0 to 30 parts by weight, more preferably 0 to 10 parts by weight, and still more preferably 0 to 2 parts by weight per 100 parts by weight of the cyclic compound represented by the formula (1).

[3] Sensitizer

The sensitizer is a component having an action that energy of the irradiated radiation is absorbed and transferred to the acid generator (C) to increase the generation amount of an acid, and improving the apparent sensitivity of the resist. As the sensitizer are mentioned, for example, benzophenones, biacetyls, pyrenes, phenothiazines, fluorenes and the like, but are not particularly limited.

These sensitizers may be used alone or in a combination of two or more. The blending amount of the sensitizer is properly adjusted depending upon the kind of the cyclic compound to be used, but is 0 to 100 parts by weight, preferably 0 to 30 parts by weight, more preferably 0 to 10 parts by weight, and still more preferably 0 to 2 parts by weight based on 100 parts by weight of the cyclic compound represented by the formula (1).

[4] Surfactant

The surfactant is a component having an action of improving the coating properties and striation of the radiation sensitive composition according to the invention, the developability of the resist and so on. Such a surfactant may be any of anionic, cationic, nonionic or ampholytic. The preferred surfactant is nonionic surfactant. The nonionic surfactant has a good affinity to the solvent used in the production of the radiation sensitive composition and is more effective. As an example of the nonionic surfactant are mentioned polyoxyethylene higher alkyl ethers, polyoxyethylene higher alkyl phenyl ethers, higher fatty acid diesters of polyethylene glycol and the like, but are not particularly limited. As a commercially available product may be mentioned tradenames: EFTOP (manufactured by Jemco Inc.), MEGAFACE (manufactured by Dai-Nippon Ink & Chemicals, Inc.), FLUORAD (manufactured by Sumitomo 3M Ltd.), ASAHIGUARD and SURFLON (both manufactured by Asahi Glass Co., Ltd.), PEPOL (manufactured by Toho Chemical Industry Co., Ltd.), KP (manufactured by Shin-Etsu Chemical Co., Ltd.), POLYFLOW (manufactured by Kyoeisha Chemical Co., Ltd.) and the like.

The blending amount of the surfactant is properly adjusted depending upon the kind of the cyclic compound to be used, but is 0 to 100 parts by weight, preferably 0 to 30 parts by weight, more preferably 0 to 10 parts by weight, and still more preferably 0 to 2 parts by weight per 100 parts by weight of the cyclic compound represented by the formula (1).

[5] Organic Carboxylic Acid, or Phosphorus Oxoacid and its Derivative

The organic carboxylic acid or phosphorus oxoacid or its derivative may be included as an optional component for the purpose of preventing the deterioration of sensitivity or improving the profile of resist pattern and the process lag stability and the like. Moreover, they may be used in combination with the acid-diffusion controller or may be used alone. As the organic carboxylic acid are preferable, for example, malonic acid, citric acid, malic acid, succinic acid, benzoic acid, salicylic acid and the like. As the phosphorus oxoacid or its derivative are mentioned, for example, phosphoric acid and its derivatives including esters such as phosphoric acid, di-n-butyl phosphate, diphenyl phosphate and the like; phosphonic acid and its derivatives including esters such as phosphonic acid, dimethyl phosphonate, di-n-butyl phosphonate, phenyl phosphonate, diphenyl phosphonate, dibenzyl phosphonate and the like; and phosphinic acid and its derivatives including esters such as phosphinic acid, phenyl phosphinate and the like. Among them, phosphoric acid is particularly preferable.

The organic carboxylic acids, or phosphorus oxoacids or their derivatives may be used alone or in a combination of two or more. The blending amount of the organic carboxylic acid, or phosphorus oxoacid or its derivative is properly adjusted depending upon the kind of the cyclic compound to be used, but is 0 to 100% by weight, preferably 0 to 30% by weight, more preferably 0 to 10% by weight, and still more preferably 0 to 2% by weight per 100 parts by weight of the cyclic compound represented by the formula (1).

[6] Additives Other than the Solubility Controller, Sensitizer, Surfactant, Organic Carboxylic Acid, Phosphorus Oxoacid and its Derivative If necessary, one or more of additives other than the solubility controller, sensitizer, and surfactant may be further blended into the radiation sensitive composition according to the invention within a range not damaging the object of the invention. As such additives are mentioned, for example, a dye, a pigment, an adhesion promoter and the like. For example, the dye and pigment are preferable because they visualize the latent image of the exposed area to reduce the influence of halation during exposure when the dye or pigment is compounded. Also, the adhesion promoter is preferable because the adhesion to a substrate can be improved when it is compounded. As another additive may be further mentioned a halation inhibitor, a storage stabilizer, a defoaming agent, a shape improver and the like, which include specifically 4-hydroxy-4'-methylchalcone and so on.

The blend in the radiation sensitive composition of the invention (cyclic compound/acid generator (C)/acid crosslinking agent (G)/acid-diffusion controller (E)/optional component (F)) is, when expressed by weight percentage based on solid, preferably 50-99.489/0.001-50/0.5-50/0.01-50/0-50, more preferably 50-99.489/0.001-50/0.5-40/0.01-5/0-15, still more preferably 60-70/10-25/1-30/0.01-3/0-1, and particularly preferably 60-70/10-25/2-20/0.01-3/0. With the above blend, the performances such as sensitivity, resolution, alkali developability and the like are excellent.

If the optional component (F) is not included, the composition of the total solids in the radiation sensitive composition of the invention is preferably (A): 3 to 96.9% by weight, (C): 0.1 to 30% by weight, (G): 0.3 to 96.9% by weight and (E): 0.01 to 30% by weight ((A)+(C)+(G)+(E)=100% by weight), more preferably (A): 65 to 96.9% by weight, (C): 0.1 to 32% by weight, (G): 0.3 to 34.9% by weight and (E): 0.01 to 30% by weight ((A)+(C)+(G)+(E)=100% by weight), still more preferably (A): 70 to 96.9% by weight, (C): 0.1 to 27% by weight, (G): 3.0 to 29.9% by weight and (E): 0.01 to 30% by weight ((A)+(C)+(G)+(E)=100% by weight), particularly preferably (A): 80 to 96.9% by weight, (C): 0.1 to 17% by weight, (G): 3.0 to 19.9% by weight and (E): 0.01 to 30% by weight ((A)+(C)+(G)+(E)=100% by weight), and most preferably (A): 90 to 96.9% by weight, (C): 0.1 to 7% by weight, (G): 3.0 to 9.9% by weight and (E): 0.01 to 30% by weight ((A)+(C)+(G)+(E)=100% by weight). Within the above range, the performances such as sensitivity, resolution, alkali developability and so on are excellent.

The radiation sensitive composition according to the invention is usually prepared by dissolving each component in a solvent to form a uniform solution and then, if necessary, filtering the solution with, for example, a filter having a pore diameter of about 0.2 μm or the like.

As the solvent used in the preparation of the radiation sensitive composition of the invention are mentioned, for example, ethylene glycol monoalkyl ether acetates such as ethylene glycol monomethyl ether acetate, ethylene glycol monoethyl ether acetate, ethylene glycol mono-n-propyl ether acetate, ethylene glycol mono-n-butyl ether acetate and the like; ethylene glycol monoalkyl ethers such as ethylene glycol monomethyl ether, ethylene glycol monoethyl ether and the like; propylene glycol monoalkyl ether acetates such as propylene glycol monomethyl ether acetate, propylene glycol monoethyl ether acetate, propylene glycol mono-n-propyl ether acetate, propylene glycol mono-n-butyl ether acetate and the like; propylene glycol monoalkyl ethers such as propylene glycol monomethyl ether, propylene glycol monoethyl ether and the like; lactic esters such as methyl lactate, ethyl lactate, n-propyl lactate, n-butyl lactate, n-amyl lactate and the like; aliphatic carboxylic esters such as methyl acetate, ethyl acetate, n-propyl acetate, n-butyl acetate, n-amyl acetate, n-hexyl acetate, methyl propionate, ethyl propionate and the like; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutyl acetate, 3-methyl-3-methoxybutyl acetate, butyl 3-methoxy-3-methylpropionate, butyl 3-methoxy-3-methyl butyrate, methyl acetoacetate, methyl pyruvate, ethyl pyruvate and the like; aromatic hydrocarbons such as toluene, xylene and the like; ketones such as 2-heptanone, 3-heptanone, 4-heptanone, cyclopentanone, cyclohexanone and the like; amides such as N,N-dimethylformamide, N-methylacetamide, N,N-dimethylacetamide, N-methylpyrrolidone and the like; lactones such as γ-lactone and the like, but not particularly limited. These solvents may be use alone or in a combination of two or more.

The radiation sensitive composition according to the invention may contain a resin soluble in an aqueous alkali solution within a range not damaging the object of the invention. As the resin soluble in an aqueous alkali solution are mentioned novolak resin, polyvinylphenols, polyacrylic acid, polyvinyl alcohol, styrene-maleic anhydride resin, polymers containing acrylic acid, vinyl alcohol or vinylphenol as a monomer unit, and derivatives thereof. The blending amount of the resin soluble in an aqueous alkali solution is properly adjusted depending upon the kind of the cyclic compound to be used, but is preferably not more than 30 parts by weight, more preferably not more than 10 parts by weight, still more preferably not more than 5 parts by weight, and particularly preferably 0 part by weight per 100 parts by weight of the cyclic compound.

[Method of Forming Resist Pattern]

The invention relates to a method of forming a resist pattern comprising a step of forming a resist film on a substrate using the above radiation sensitive composition according to the invention, a step of exposing the resist film to radiation, and a step of developing the resist film to form a resist pattern. The resist pattern of the invention can be also formed as an upper layer resist in the multilayer resist process.

In the formation of the resist pattern, the radiation sensitive composition of the invention is applied onto a conventionally-known substrate by a coating means such as spin coating, cast coating, roll coating or the like to form a resist film. The conventionally-known substrate is not particularly limited and may be exemplified by substrates for electronic parts, substrates having the predetermined wiring pattern formed thereon and so on. More specifically, a silicon wafer, substrates made from metal such as copper, chromium, iron and aluminum, glass substrate and the like are mentioned. As a material for the wiring pattern are mentioned, for example, copper, aluminum, nickel, gold and so on. The substrate may be provided with an inorganic-based and/or organic-based film, if necessary. As the inorganic-based film, an inorganic anti-reflection coating (inorganic BARC) is mentioned. As the organic-based film, an organic anti-reflection coating (organic BARC) is mentioned. A surface treatment with hexamethylene disilazane or the like may be conducted on the substrates.

Then, the coated substrate is heated, if necessary. The heating condition varies according to the composition of the radiation sensitive composition and the like, but is preferably 20 to 250° C., more preferably 20 to 150° C. It is preferable that the adhesion of the resist to the substrate may be improved by the heating. Then, the resist film is exposed in a desired pattern to any of radiation selected from the group consisting of visible light, ultraviolet ray, excimer laser, electron beams, extreme ultraviolet ray (EUV), X-ray and ion beams. The exposing conditions are suitably selected according to the composition of the radiation sensitive composition and the like. In the invention, it is preferred to conduct a heat treatment after the irradiation of radiation in order to stably form high accuracy fine patterns by the exposure. The heating condition varies depending upon the composition of the radiation-sensitive composition, but is preferably 20 to 250° C., more preferably 20 to 150° C.

Then, the exposed resist film is developed with an alkali developing solution to form the desired resist pattern. As the alkali developing solution, an aqueous alkaline solution formed, for example, by dissolving at least one alkaline compound selected from mono-, di- or tri-alkylamines, mono-, di- or tri-alkanolamines, heterocyclic amines, tetramethylammonium hydroxide (TMAH), choline and the like so as to have a concentration of preferably 1 to 10% by mass, more preferably 1 to 5% by mass, is used. It is preferable that when the concentration in the aqueous alkaline solution is not more than 10% by mass, the dissolution of the exposed portion in the developing solution can be suppressed.

Furthermore, an appropriate amount of an alcohol such as methanol, ethanol, isopropyl alcohol or the like, or the aforementioned surfactant may be added to the alkali developing solution. Among them, the addition of 10 to 30% by mass of isopropyl alcohol is particularly preferable. Thus, the wettability of the developing solution to the resist can be enhanced. If the developing is conducted with the developing solution made of the aqueous alkaline solution, the resist pattern is generally washed with water after the developing.

After the formation of the resist pattern, the substrate is etched to obtain a patterned wiring board. The etching may be performed by a well-known method such as dry-etching with a plasma gas, wet-etching with an alkali solution, a cupric chloride solution, a ferric chloride solution or the like, and so on.

After the formation of the resist patterns, plating may also be conducted. As the plating method, there are, for example, copper plating, solder plating, nickel plating, gold plating and the like.

The remaining resist patterns after the etching can be peeled off with an organic solvent or an alkaline aqueous solution stronger than the aqueous alkali solution used for the development. As the organic solvent are mentioned PGMEA (propylene glycol monomethyl ether acetate), PGME (propylene glycol monomethyl ether), EL (ethyl lactate) and the like. As the strong alkaline aqueous solution are mentioned, for example, an aqueous solution of 1 to 20% by mass of sodium hydroxide and an aqueous solution of 1 to 20% by mass of potassium hydroxide. As the peeling method are mentioned, for example, dipping method, spraying method and the like. The wiring board having the resist patterns formed thereon may be a multi-layered wiring board and may have small diameter through-holes.

The wiring board obtained by the invention may be also produced by a method wherein a metal is deposited under vacuum after the formation of the resist pattern and then the resist pattern is dissolved with a solution, i.e., a lift-off method.

EXAMPLE

The embodiments of the invention will be described in more detail with reference to the examples below. However, the invention is not limited to these examples. In the following synthesis examples and examples, the structure of each compound is identified with $^1$H-NMR measurement.

Synthesis Example 1

Synthesis of 4-biphenylaldehyde pentaerythritol acetal 200 g (1.47 mol) of pentaerythritol is dissolved in 2000 mL of DMF and the temperature is raised to 100° C. in a mantle heater for dissolving crystals. 20 g (0.105 mol) of p-toluene sulfonic acid dihydrate is added, and a solution of 134 g (73.6 mol) of 4-biphenyl aldehyde dissolved in 700 mL of toluene is added dropwise to the solution, and then the temperature is raised to 145° C. At the time that the internal temperature reaches to 140° C., reflux is started with a Dimroth condenser. During the reflux, water is separated with a Dean-stark apparatus. After 5 hours, the reaction product is diluted with 5 L of distilled water, and the precipitated white crystals are filtered to separate. After washed with distilled water, 160 g of the resulting white crystals is dissolved in tetrahydrofuran/water=1.2 L/3 L under heating and filtered to remove remaining insoluble dimers. After the concentration of the solution, the resulting product is dispersed in ethyl acetate and filtered to obtain white crystals (123 g, % yield).

The analytical result with LC-MS shows that the compound is a target with a molecular weight of 300. Also, chemical shift values (δ ppm, TMS reference) of $^1$H-NMR in heavy dimethyl sulfoxide are 3.3-4.0 (m, 8H), 4.4-4.7 (m, 2H), 5.4 (s, 1H) and 7.2-8.7 (m, 9H).

Synthesis Example 2

Synthesis of 4-bicyclohexylaldehyde pentaerythritol acetal

Into an autoclave are charged 364 g (1.21 mol) of 4-biphenylaldehyde pentaerythritol acetal synthesized in Synthesis Example 1, 910 g of isopropanol and 7.28 g of Ru 5%/Al$_2$O$_3$ catalyst (manufactured by N. E. CAMCAT), which are reacted at 160° C. for 5 hours under hydrogen of 10 MPa and then cooled. The catalyst is filtered off under an inert gas atmosphere, and then the solvent is distilled off in an evaporator. Thus, white crystals (186 g, 58% crude yield) are obtained.

186 g of the white crystals is dispersed into 1 L of toluene, which is stirred at 60° C. for 30 minutes. After the cooling, 155 g of white crystals is obtained through filtration. This operation is repeated again to obtain white crystals (113 g, 35% yield).

The analytical result with LC-MS shows that the compound is a target with a molecular weight of 264. Also, chemical shift values (δ ppm, TMS reference) of $^1$H-NMR in heavy dimethyl sulfoxide are 0.7-1.8 (m, 20H) and 3.1-4.7 (m, 12H).

Synthesis Example 3

Synthesis of Cyclic Compound (A)

Synthesis of CR-1A

Into a four-necked flask (300 mL) equipped with a dropping funnel, a Dimroth condenser, a thermometer and stirring blades, which is sufficiently dried and purged with nitrogen, are charged resorcinol (3.70 g, 0.0336 mol, manufactured by Kanto Chemical Co., Inc.), dehydrated ethanol (32 mL) and 5.18 mL of concentrated hydrochloric acid (35%) under nitrogen stream to prepare an ethanol solution. Then, 4-bicyclohexylaldehydepentaerythritol acetal (10.0 g, 0.0320 mol) dissolved in 60 mL of ethanol is added dropwise from a dropping funnel over 10 minutes, and the resulting solution is heated to 80° C. in a mantle heater with stirring. The solution is continuously stirred at 80° C. for 5 hours. After the completion of the reaction, the solution is left to stand to reach room temperature. Target crude crystals are produced and filtered to separate after the reaction, and added with 200 mL of distilled water. After the filtration, the crude crystals are washed with 200 ml of distilled water four times, filtered and dried under vacuum to obtain the target product (hereinafter referred to as CR-1A) (13.5 g, 58% yield).

The analytical result with LC-MS shows that the compound is a target with a molecular weight of 1146. Also, chemical shift values (δ ppm, TMS reference) of $^1$H-NMR in heavy dimethyl sulfoxide are 0.5-2.0 (m, 84H), 6.0-6.2 (m, 4H), 6.8-6.3 (m, 4H), 8.2-9.5 (m, 4H) and 9.6 (s, 8H).

[Chem. 45]

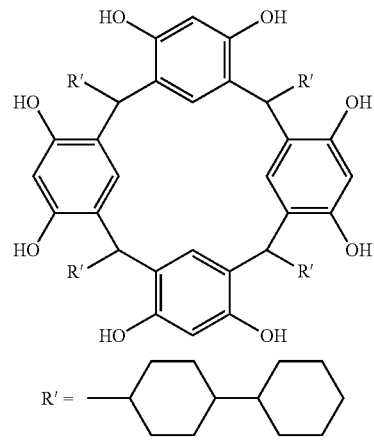

Comparative Synthesis Example 1

Synthesis of CR-2A

Into a four-necked flack (2000 mL) equipped with a dropping funnel, a Dimroth condenser, a thermometer and stirring blades, which is sufficiently dried and purged with nitrogen, are charged resorcinol (120 g, 1.09 mol, manufactured by Kanto Chemical Co., Inc.), dehydrated ethanol (1.36 L) and 168 mL of concentrated hydrochloric acid (35%) under nitrogen stream to prepare an ethanol solution. Then, 4-cyclohexylbenzaldehyde (196 g, 1.04 mol) is added dropwise from a dropping funnel over 10 minutes, and the resulting solution is heated to 80° C. in a mantle heater with stirring. The solution is continuously stirred at 80° C. for 5 hours. After the completion of the reaction, the solution is left to stand to reach room temperature. Target crude crystals are produced and filtered after the reaction, and 1000 mL of distilled water is added thereto. After the filtration, the crude crystals are washed with 1000 ml of distilled water six times, filtered and dried under vacuum to obtain the target product (hereinafter referred to as CR-2A) (278 g, 91% yield).

The analytical result with LC-MS shows that the compound is a target with a molecular weight of 1122. Also, chemical shift values (δ ppm, TMS reference) of $^1$H-NMR in heavy dimethyl sulfoxide are 0.8-1.9 (m, 44H), 5.5-5.6 (d, 4H), 6.0-6.8 (m, 24H) and 8.4-8.5 (m, 8H).

[Chem. 46]

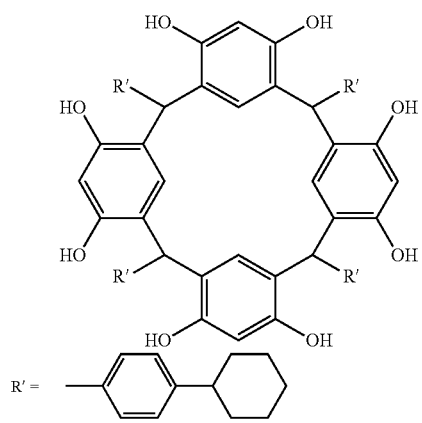

Example 1 and Comparative Example 1

(1) Solubility Test of the Compounds in Safety Solvents

The dissolved amounts of the compounds obtained in Synthesis Example 3 and Comparative Synthesis Example 1 in propylene glycol monomethyl ether acetate (PGMEA), propylene glycol monomethyl ether (PGME) and cyclohexanone are evaluated. The results are shown in Table 1.

A: 5.0 wt %≤dissolved amount
B: dissolved amount<5.0 wt %

TABLE 1

| | Compound | PGMEA | PGME | CHN |
|---|---|---|---|---|
| Example 1 | CR-1A | A | A | A |
| Comparative Example 1 | CR-2A | B | A | B |

INDUSTRIAL APPLICABILITY

The invention is suitably used for the cyclic compound having a specific chemical structure and useful as the acid-amplified, non-polymer resist material, the radiation sensitive composition containing the same, and the method of forming a resist pattern using the radiation sensitive composition.

The invention claimed is:
1. A cyclic compound represented by the following formula (1):

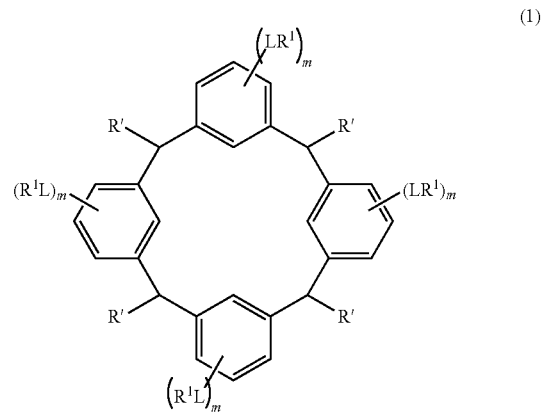

in the formula (1),
L is independently a divalent group selected from the group consisting of a single bond, a linear or branched alkylene group having a carbon number of 1 to 20, a cycloalkylene group having a carbon number of 3 to 20, an arylene group having a carbon number of 6 to 24, —O—, —OC(=O)—, —OC(=O)O—, —N(R$^5$)—C(=O)—, —N(R$^5$)—C(=O)O—, —S—, —SO, —SO$_2$— and any combination thereof;
R$^1$ is independently an alkyl group having a carbon number of 1 to 20, a cycloalkyl group having a carbon number of 3 to 20, an aryl group having a carbon number of 6 to 20, an alkoxyl group having a carbon number of 1 to 20, cyano group, nitro group, hydroxyl group, heterocyclic group, halogen, carboxyl group, an acyl group having a carbon number of 2 to 20, an alkylsilyl group having a carbon number of 1 to 20, or hydrogen atom, with the proviso that at least one R$^1$ is a hydrogen atom; and
R' is independently represented by the following formula (1-2):

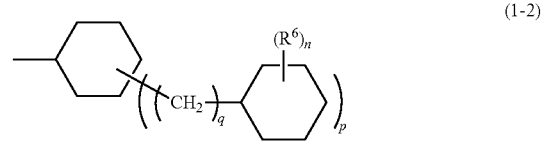

in the formula (1-2),
R$^6$ is a hydrogen atom or a group selected from the group consisting of an alkyl group having a carbon number of 1 to 12, a cycloalkyl group having a carbon number of 3 to 12, an aryl group having a carbon number of 6 to 12, an alkoxy group having a carbon number of 1 to 12, cyano group, nitro group, heterocyclic group, halogen, carboxyl group, hydroxyl group and an alkylsilyl group having a carbon number of 1 to 12;
n is an integer of 0 to 5;
p is an integer of 0 to 5; and
q is an integer of 0 to 5;

$R^5$ is hydrogen or an alkyl group having a carbon number of 1 to 10; and m is independently an integer of 1 to 4.

2. The cyclic compound according to claim 1, which is represented by the following formula (2):

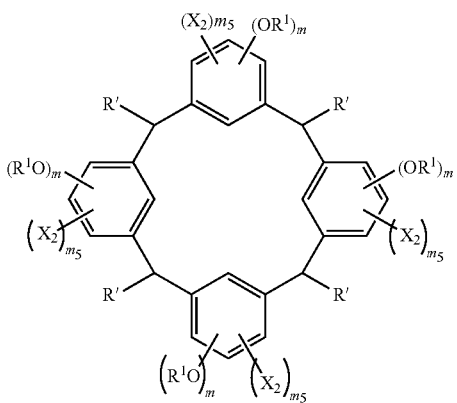

(2)

in the formula (2), $R^1$, R' and m are the same as described above;

$X_2$ is a hydrogen or halogen atom;

$m_5$ is independently an integer of 0 to 3; and $m+m_5=4$.

3. The cyclic compound according to claim 1, which is represented by the following formula (3):

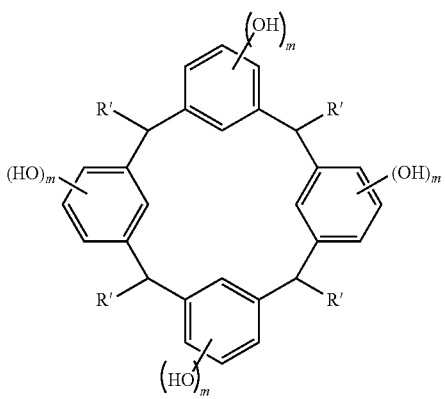

(3)

in the formula (3), R' and m are the same as described above.

4. The cyclic compound according to claim 1, wherein R' is independently represented by the following formula (1-4):

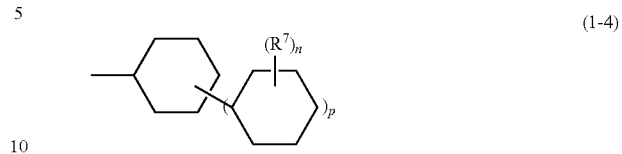

(1-4)

in the formula (1-4), $R^7$ is a group selected from the group consisting of an alkyl group having a carbon number of 1 to 12, a cycloalkyl group having a carbon number of 3 to 12, an aryl group having a carbon number 6 to 12, an alkoxy group having a carbon number of 1 to 12, cyano group, nitro group, heterocyclic group, halogen, carboxyl group, hydroxyl group and an alkylsilyl group having a carbon number of 1 to 12;

n is an integer of 0 to 5; and p is an integer of 0 to 5.

5. The cyclic compound according to claim 1, wherein R' is independently represented by the following formula (1-5):

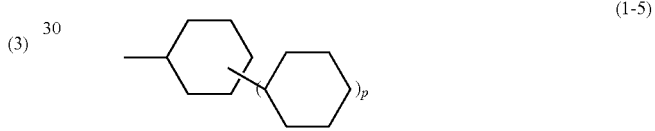

(1-5)

in the formula (1-5), p is an integer of 0 to 5.

6. A method of producing a cyclic compound represented by the formula (1), which comprises condensation-reacting one or more selected from carbonyl compounds (A1) with one or more selected from phenolic compounds (A2).

7. A method of producing a cyclic compound represented by the formula (1), which comprises condensation-reacting one or more selected from acetal compounds (A4) of carbonyl compounds (A1) with one or more selected from phenolic compounds (A2).

* * * * *